(12) United States Patent
Wagner et al.

(10) Patent No.: US 8,211,923 B2
(45) Date of Patent: Jul. 3, 2012

(54) SUBSTITUTED ARYLSULFONYLAMINO-METHYLPHOSPHONIC ACID DERIVATIVES, THEIR PREPARATION AND THEIR USE IN THE TREATMENT OF TYPE I AND II DIABETES MELLITUS

(75) Inventors: Holger Wagner, Mettenberg (DE); Elke Langkopf, Warthausen (DE); Matthias Eckhardt, Biberach (DE); Ruediger Streicher, Biberach (DE); Corinna Schoelch, Mittlebiberach (DE); Annette Schuler-Metz, Ulm (DE); Alexander Pautsch, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 40 days.

(21) Appl. No.: 12/669,979

(22) PCT Filed: Jul. 25, 2008

(86) PCT No.: PCT/EP2008/059807
§ 371 (c)(1),
(2), (4) Date: Apr. 1, 2010

(87) PCT Pub. No.: WO2009/016119
PCT Pub. Date: Feb. 5, 2009

(65) Prior Publication Data
US 2010/0210595 A1      Aug. 19, 2010

(30) Foreign Application Priority Data

Jul. 27, 2007   (DE) .................. 10 2007 035 334

(51) Int. Cl.
| | |
|---|---|
| *A61K 31/404* | (2006.01) |
| *A61K 31/416* | (2006.01) |
| *A61K 31/4184* | (2006.01) |
| *A61K 31/423* | (2006.01) |
| *A61K 31/428* | (2006.01) |
| *C07D 277/62* | (2006.01) |
| *C07D 263/54* | (2006.01) |
| *C07D 235/04* | (2006.01) |
| *C07D 231/56* | (2006.01) |
| *C07D 209/04* | (2006.01) |

(52) U.S. Cl. ........ 514/367; 514/394; 514/406; 514/415; 548/152; 548/217; 548/304.4; 548/361.1; 548/469; 548/486; 548/490

(58) Field of Classification Search .................. 548/152, 548/217, 304.4, 361.1, 469, 486, 490
See application file for complete search history.

(56) References Cited

U.S. PATENT DOCUMENTS

| | | | |
|---|---|---|---|
| 6,812,250 B2 | 11/2004 | Defossa et al. | |
| 7,138,414 B2 | 11/2006 | Schoenafinger et al. | |
| 7,223,796 B2 | 5/2007 | Defossa et al. | |
| 7,262,220 B2 | 8/2007 | Defossa et al. | |
| 7,989,622 B2 | 8/2011 | Bajjalieh et al. | |
| 2006/0142250 A1 | 6/2006 | Blaskovich et al. | |
| 2010/0093703 A1 | 4/2010 | Wagner et al. | |
| 2010/0130557 A1 | 5/2010 | Wagner et al. | |
| 2010/0210594 A1 | 8/2010 | Wagner et al. | |
| 2010/0210595 A1 | 8/2010 | Wagner et al. | |

FOREIGN PATENT DOCUMENTS

| | | |
|---|---|---|
| EP | 0604657 A1 | 7/1994 |
| EP | 0638581 A1 | 2/1995 |
| EP | 1074542 A1 | 2/2001 |
| JP | 2005206492 A | 8/2005 |
| WO | 9928297 A1 | 6/1999 |
| WO | 0170754 A1 | 9/2001 |
| WO | 02096864 A1 | 12/2002 |
| WO | 03084922 A1 | 10/2003 |
| WO | 2004007437 A1 | 1/2004 |
| WO | 2004007455 A1 | 1/2004 |
| WO | 2004104001 A2 | 12/2004 |
| WO | 2005/013976 A1 | 2/2005 |
| WO | 2005/013977 A1 | 2/2005 |
| WO | 2005/013978 A1 | 2/2005 |
| WO | 2005/024535 A2 | 3/2005 |
| WO | 2006034418 A2 | 3/2006 |
| WO | 2006052722 A1 | 5/2006 |
| WO | 2007044729 A2 | 4/2007 |
| WO | 2008/099000 A2 | 8/2008 |
| WO | 2008/103354 A2 | 8/2008 |
| WO | 2008/113760 A2 | 9/2008 |
| WO | 2009/016118 A1 | 2/2009 |
| WO | 2009/016119 A1 | 2/2009 |

(Continued)

OTHER PUBLICATIONS

International Search Report for PCT/EP2008/059807 mailed Nov. 12, 2008.

(Continued)

*Primary Examiner* — Shawquia Young
(74) *Attorney, Agent, or Firm* — Michael P. Morris; David L. Kershner; Usha R. Patel

(57) ABSTRACT

The present invention relates to substituted arylsulphonylaminomethyl-phosphonic acid derivatives of general formula

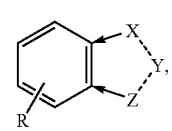

(I)

wherein R, X, Y and Z are defined as in claim 1, the tautomers, enantiomers, diastereomers, mixtures thereof and salts thereof which have valuable pharmacological properties, particularly the suppression of the interaction of glycogen phosphorylase a with the $G_L$ subunit of glycogen-associated protein phosphatase 1 (PP1), and their use as pharmaceutical compositions.

12 Claims, No Drawings

FOREIGN PATENT DOCUMENTS

WO   2009030715 A1   3/2009

OTHER PUBLICATIONS

U.S. Appl. No. 12/530,507, filed Dec. 4, 2009.
U.S. Appl. No. 12/527,249, filed Oct. 8, 2009.
U.S. Appl. No. 12/669,978, filed Jan. 21, 2010.
U.S. Appl. No. 12/669,979, filed Jan. 21, 2010.
Abstract in English for JP200506492 cited herein.
International Search Report for PCT/EP2008/061651 mailed Dec. 1, 2008.
Martin, Yvonne C. et al. "Do Structurally Similar Molecules Have Similar Biological Activity?" 45 J. Med. Chem. pp. 4350-4358 (2002).
Chen, et al. "Discovering Benzamide Derivatives as Glycogen Phosphorylase Inhibitors and Their Binding Site at the Enzyme" 15 Bioorg. & Med. Chem. pp. 6763-6774 (2007).
Jordan, V Craig, "Tamoxifen: A Most Unlikely Pioneering Medicine"Nature Reviews Drug Discovery, vol. 2, Mar. 2003, pp. 205-213.
Cohen, Philip "The Twentieth Centry Struggle to Decipher Insulin Signalling" Nature Reviews Molecular Cell Biology, vol. 7, Nov. 2006, pp. 867-874.
Zibrova, Darya et al., "Inhibition of the interaction between protein phosphatase 1 glycogen-targeting subunit and glycogen phosphorylase increases glycogen synthesis in primary rat hepatocytes" Biochem Journal, 2008, 412, pp. 359-365.
WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pp. 681. This PCT publication is too large for EFS submission via the foreign patent section, therefore submitting in two parts in the NPL section. pp. 1-340.
WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pp. 681. This PCT publication is too large for EFS submission via the foreign patent section, therefore submitting in two parts in the NPL section. pp. 341-681.

SUBSTITUTED ARYLSULFONYLAMINO-METHYLPHOSPHONIC ACID DERIVATIVES, THEIR PREPARATION AND THEIR USE IN THE TREATMENT OF TYPE I AND II DIABETES MELLITUS

This application is the national stage filing under 35 U.S.C. §371 International Application No. PCT/EP2008/059807, filed Jul. 25, 2008, which claims the benefit of German Application No. DE102007035334.2, filed Jul. 27, 2007, each of which is incorporated by reference in its entirety.

The present invention relates to substituted arylsulphonylaminomethyl-phosphonic acid derivatives of general formula I

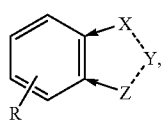

(I)

wherein the groups R, X, Y and Z are defined as hereinafter, including the tautomers, stereoisomers, mixtures thereof and salts thereof. This invention further relates to pharmaceutical compositions containing a compound of formula I according to the invention as well as the use of a compound according to the invention for preparing a pharmaceutical composition for the treatment of metabolic disorders, particularly type 1 or type 2 diabetes mellitus. The invention also relates to processes for preparing a pharmaceutical composition as well as a compound according to the invention.

Compounds of formula I are suitable for preventing the inhibiting effect of glycogen phosphorylase on the activity of glycogen synthase by stopping the interaction of glycogen phosphorylase a with the $G_L$ subunit of glycogen-associated protein phosphatase 1 (PP1). Compounds with these properties stimulate glycogen synthesis and are proposed for the treatment of metabolic disorders, particularly diabetes (P. Cohen, *Nature Reviews Molecular Cell Biology* 2006, 7, 867-874).

Aim of the Invention

The aim of the present invention is to provide new arylsulphonylamino-methylphosphonic acid derivatives that suppress the interaction of glycogen phosphorylase a with the $G_L$ subunit of glycogen-associated protein phosphatase 1 (PP1).

A further aim of the present invention is to provide new pharmaceutical compositions that are suitable for the prevention and/or treatment of metabolic disorders, particularly diabetes.

Another aim of this invention is to provide a process for preparing the compounds according to the invention.

Other aims of the present invention will become directly apparent to the skilled man from the foregoing remarks and those that follow.

OBJECT OF THE INVENTION

In a first aspect the present invention relates to new substituted arylsulphonylamino-methylphosphonic acid derivatives of general formula

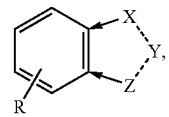

(I)

wherein
R denotes a group of formula

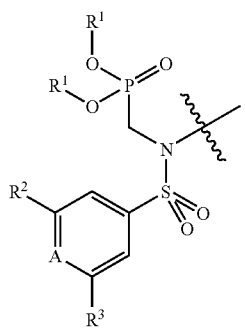

wherein
R$^1$ denotes H, C$_{1-6}$-alkyl-carbonyl-oxy-C$_{1-3}$-alkyl or C$_{1-6}$-alkoxy-carbonyl-oxy-C$_{1-3}$-alkyl, R$^2$ and R$^3$ independently of one another denote H, halogen, C$_{1-3}$-alkyl, C$_{1-3}$-perfluoralkyl, C$_{1-3}$-perfluoroalkoxy, C$_{1-3}$-alkoxy, cyano, nitro or hydroxy and A denotes CH or N, and the heterocyclic group

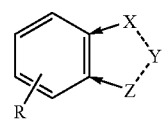

denotes a group of formula

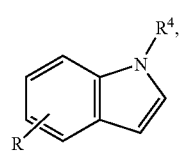

(Ia)

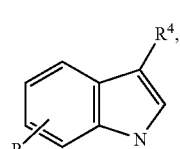

(Ib)

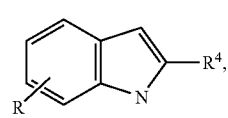

(Ic)

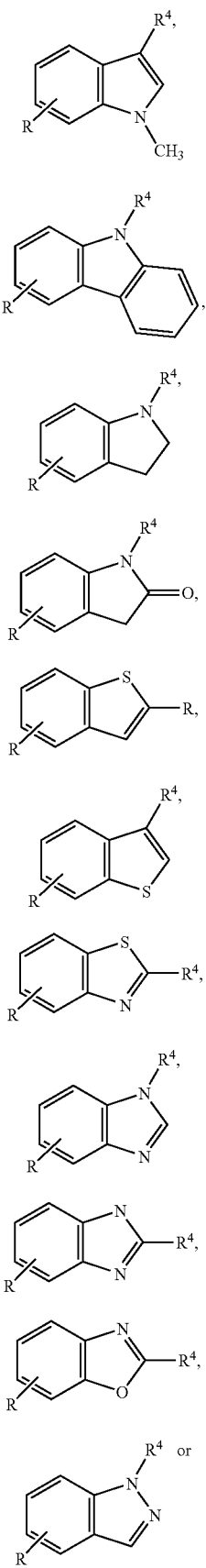

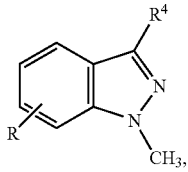

wherein the above-mentioned heterocycles of formula n (Ia), (Ib), (Ic), (Id), (If), (Ig), (Ih), (Ii), (Ik) and (Io) may optionally be substituted at the carbon atoms of the 5 ring in each case by a group selected from among $C_{1-3}$-alkyl, cyano, $C_{1-3}$-perfluoralkyl, $C_{3-6}$-cycloalkyl, $C_{1-3}$-alkyl-carbonyl, $C_{1-3}$-Perfluoralkyl-carbonyl, carboxyl, aminomethyl, $C_{1-3}$-alkyl-aminomethyl, di-($C_{1-3}$-alkyl)-aminomethyl, $C_{1-3}$-alkyl-carboxyl, carboxy-$C_{1-3}$-alkyl, aminocarbonyl, $C_{1-3}$-alkyl-aminocarbonyl or di-($C_{1-3}$-alkyl)-aminocarbonyl and $R^4$ denotes H, $C_{1-6}$-alkyl, $C_{1-6}$-alkyl-carbonyl, cyano, carboxyl, $C_{1-6}$-alkoxy-carbonyl, phenylcarbonyl, 5-chloro-1H-indol-2-yl-carbonyl, aminocarbonyl, $C_{1-6}$-alkyl-aminocarbonyl, di-($C_{1-6}$-alkyl)-aminocarbonyl, $C_{3-6}$-cycloalkyl-aminocarbonyl, N—($C_{3-6}$-cycloalkyl)-N—($C_{1-6}$-alkyl)-aminocarbonyl, morpholin-4-yl-carbonyl, piperazin-1-yl-carbonyl, 4-($C_{1-3}$-alkyl)-piperazin-1-yl-carbonyl, aryl-amino-carbonyl, N-oxy-pyridylamino-carbonyl, aminocarbonyl-carbonyl, $C_{1-3}$-alkylaminocarbonyl-carbonyl, di-($C_{1-3}$-alkyl)-aminocarbonyl-carbonyl, pyrrolidinylcarbonyl-carbonyl, piperidinylcarbonyl-carbonyl, morpholinylcarbonyl-carbonyl, piperazinylcarbonyl-carbonyl, 4-methyl-piperazin-1-ylcarbonyl-carbonyl, $C_{1-3}$-alkyl-sulphonyl or phenyl-sulphonyl, while the $C_{1-6}$-alkyl group mentioned above in the definition of $R^4$ may be substituted by phenyl or phenyl-sulphonyl, the $C_{1-6}$-alkyl-carbonyl group mentioned above in the definition of $R^4$ may be substituted in the alkyl moiety by di-($C_{1-3}$-alkyl)-amino, pyrrolidin-1-yl, piperidin-1-yl, morpholin-4-yl, piperazin-1-yl, 4-methyl-piperazin-1-yl or phenyl, the $C_{1-6}$-alkyl-aminocarbonyl, di-($C_{1-6}$-alkyl)-aminocarbonyl and N—($C_{3-6}$-cycloalkyl)-N—($C_{1-6}$-alkyl)-aminocarbonyl groups mentioned above in the definition of $R^4$ may each be substituted in the alkyl moiety by $C_{1-3}$-alkyl-amino, di-($C_{1-3}$-alkyl)-amino, $C_{3-6}$-cycloalkyl-amino, N—($C_{3-6}$-cycloalkyl)-N—($C_{1-6}$-alkyl)-amino, pyrrolidin-1-yl, piperidin-1-yl, morpholin-4-yl, piperazin-1-yl, 4-methyl-piperazin-1-yl or methylaminocarbonyl, the aryl moiety of the aryl-amino-carbonyl groups mentioned above in the definition of $R^4$ is a 6-membered aromatic system which contains 0 to 3 nitrogen atoms and may be substituted by nitro, the $C_{1-6}$-alkyl groups of the di-($C_{1-6}$-alkyl)-aminocarbonyl groups mentioned above in the definition of $R^4$, together with the nitrogen atom to which they are bound, may form a saturated 4- to 7-membered ring system, which may be substituted by hydroxy, and the $C_{1-3}$-alkyl-sulphonyl group mentioned above in the definition of $R^4$ may be substituted by phenyl in the alkyl moiety.

The invention also relates to the tautomers, stereoisomers, mixtures and salts, particularly the physiologically acceptable salts, of the compounds according to the invention.

The compounds of general formula I according to the invention and the physiologically acceptable salts thereof have valuable pharmacological properties, in particular they suppress the interaction of glycogen phosphorylase a with the $G_L$-subunit of glycogen-associated protein phosphatase 1 (PP1).

Therefore this invention also relates to the use of the compounds according to the invention, including the physiologically acceptable salts, as pharmaceutical compositions.

The compounds of the above general formula I, wherein $R^1$ does not represent hydrogen, but denotes one of the other groups specified, are so-called prodrugs. By prodrugs are meant compounds that are not active per se but are converted into the corresponding active compound in vivo, cleaving the prodrug group.

This invention further relates to pharmaceutical compositions containing at least one compound according to the invention or a physiologically acceptable salt according to the invention, optionally together with one or more inert carriers and/or diluents.

A further object of this invention is the use of at least one compound according to the invention or a physiologically acceptable salt of such a compound for preparing a pharmaceutical composition that is suitable for the treatment or prevention of diseases or conditions that can be influenced by suppressing the interaction of glycogen phosphorylase a with the $G_L$-subunit of glycogen-associated protein phosphatase 1 (PP1).

The invention also relates to the use of at least one compound according to the invention for preparing a pharmaceutical composition which is suitable for the treatment of metabolic disorders, for example type I or II diabetes mellitus.

The invention also relates to the use of at least one compound according to the invention for preparing a pharmaceutical composition for suppressing the interaction of glycogen phosphorylase a with the $G_L$-subunit of glycogen-associated protein phosphatase 1 (PP1).

A further object of this invention is a process for preparing a pharmaceutical composition according to the invention, characterised in that a compound according to the invention is incorporated in one or more inert carriers and/or diluents by a non-chemical method.

The present invention also relates to a process for preparing the compounds of general formula I according to the invention.

DETAILED DESCRIPTION OF THE INVENTION

Unless stated otherwise, the groups, radicals and substituents, particularly R, X, Y and Z, have the meanings given hereinbefore and hereinafter.

If groups, substituents or radicals occur more than once in a compound, they may have the same or different meanings.

Preferred compounds of the above general formula I are those wherein

R denotes a group of the above-mentioned formula wherein $R^1$ denotes H, $C_{1-6}$-alkyl-carbonyl-oxy-$C_{1-2}$-alkyl or $C_{1-6}$-alkoxy-carbonyl-oxy-$C_{1-2}$-alkyl, $R^2$ and $R^3$ independently of one another denote halogen, $C_{1-3}$-alkyl, $C_{1-3}$-perfluoroalkyl, $C_{1-2}$-alkoxy or cyano and A denotes CH or N, and the heterocyclic group

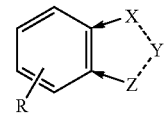

denotes a group of formula

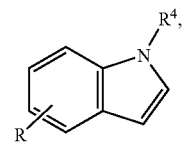

(Ia)

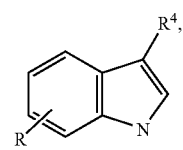

(Ib)

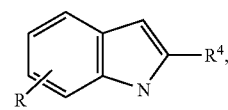

(Ic)

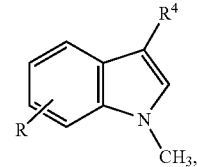

(Id)

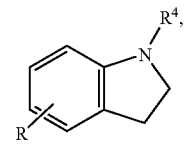

(If)

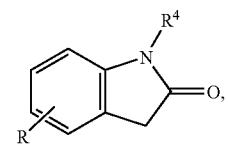

(Ig)

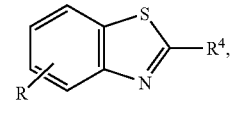

(Ij)

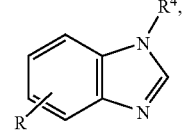

(Ik)

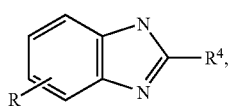 (Im)

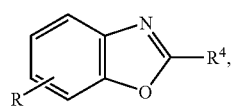 (In)

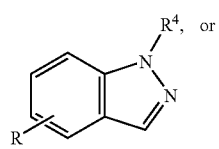 (Io)

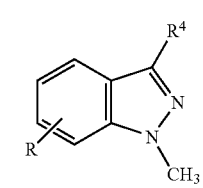 (Ip)

wherein the above-mentioned heterocycles of formulae (Ia), (If) and (Ig) may optionally be substituted at the carbon atoms of the 5 ring in each case by a group selected from among $C_{1-3}$-alkyl, $C_{1-3}$-alkyl-carbonyl or $C_{1-3}$-perfluoroalkyl-carbonyl and $R^4$ denotes H, $C_{1-4}$-alkyl, $C_{1-4}$-alkyl-carbonyl, cyano, carboxyl, $C_{1-4}$-alkoxy-carbonyl, phenylcarbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N—($C_{3-6}$-cycloalkyl)-N—($C_{1-4}$-alkyl)-amino-carbonyl, morpholin-4-yl-carbonyl, piperazin-1-yl-carbonyl, 4-(methyl)-piperazin-1-yl-carbonyl, N,N-di-($C_{1-4}$-alkyl)-amino-$C_{1-3}$-alkyl-amino-carbonyl, aryl-amino-carbonyl, $C_{1-2}$-alkyl-sulphonyl, phenyl-$C_{1-2}$-alkyl-sulphonyl or phenyl-sulphonyl, while the $C_{1-4}$-alkyl group mentioned above in the definition of $R^4$ may be substituted by phenyl, the $C_{1-4}$-alkyl-carbonyl group mentioned above in the definition of $R^4$ may be substituted in the alkyl moiety by morpholin-4-yl or phenyl, the aryl moiety of the aryl-amino-carbonyl groups mentioned above in the definition of $R^4$ is a 6-membered aromatic system which contains 0 to 2 nitrogen atoms, and the $C_{1-4}$-alkyl groups of the di-($C_{1-4}$-alkyl)-aminocarbonyl groups mentioned above in the definition of $R^4$ may form together with the nitrogen atom to which they are bound a saturated 4- to 6-membered ring system, which may be substituted by hydroxy.

Particularly preferred are those compounds of the above general formula I, wherein R denotes a group of the above-mentioned formula, wherein $R^1$ denotes H, $C_{1-4}$-alkyl-carbonyl-oxy-$C_{1-2}$-alkyl or $C_{1-4}$-alkoxy-carbonyl-oxy-$C_{1-2}$-alkyl, $R^2$ and $R^3$ independently of one another represent chlorine, bromine or $C_{1-2}$-alkyl and A denotes CH or N, and the heterocyclic group

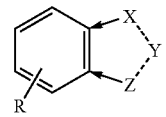

denotes a group of formula

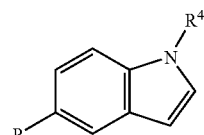 (Ia-1)

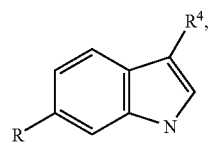 (Ib-1)

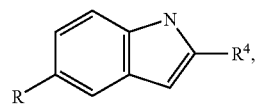 (Ic-1)

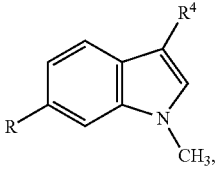 (Id-1)

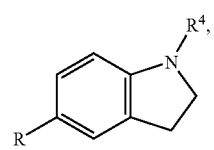 (If-1)

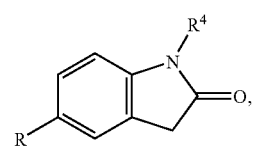 (Ig-1)

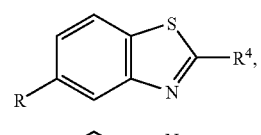 (Ij-1)

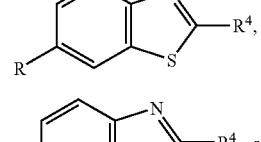 (Ij-2)

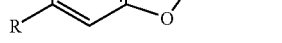 (In-1)

-continued

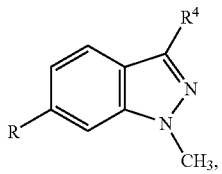
(Ip-1)

wherein the above-mentioned heterocycles of formulae (Ia) and (If) may optionally be substituted at the carbon atoms of the 5 ring in each case by a group selected from among methyl, ethyl, methylcarbonyl or trifluoromethylcarbonyl and $R^4$ denotes H, $C_{1-4}$-alkyl, benzyl, $C_{1-4}$-alkyl-carbonyl, $C_{1-4}$-alkoxy-carbonyl, phenylcarbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N—($C_{3-6}$-cycloalkyl)-N—($C_{1-4}$-alkyl)-amino-carbonyl, pyrrolidin-1-yl-carbonyl, 3-hydroxy-pyrrolidin-1-yl-carbonyl, piperidin-1-yl-carbonyl, morpholin-4-yl-carbonyl, piperazin-1-yl-carbonyl, N,N-di-($C_{1-3}$-alkyl)-amino-$C_{1-3}$-alkyl-aminocarbonyl, phenylamino-carbonyl, pyridinylamino-carbonyl, aminocarbonyl-carbonyl, benzyl-sulphonyl or phenyl-sulphonyl, while the $C_{1-4}$-alkyl-carbonyl group mentioned above in the definition of $R^4$ may be substituted in the alkyl moiety by morpholin-4-yl;

but particularly those compounds of the above general formula I, wherein

R denotes a group of the above-mentioned formula, wherein $R^1$ denotes H, $C_{1-4}$-alkyl-carbonyl-oxy-methyl or $C_{1-4}$-alkoxy-carbonyl-oxy-methyl, $R^2$ and $R^3$ independently of one another represent chlorine, bromine or methyl and A denotes CH or N, and the heterocyclic group

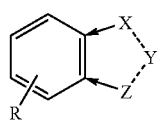

denotes a group of formula

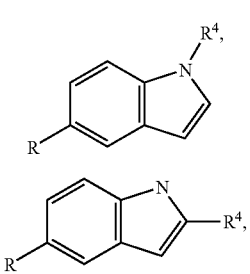
(Ia-1)

(Ic-1)

-continued

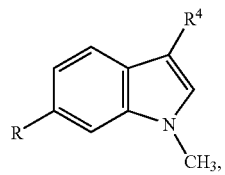
(Id-1)

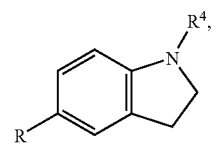
(If-1)

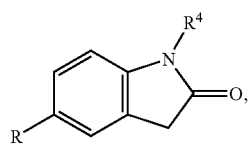
(Ig-1)

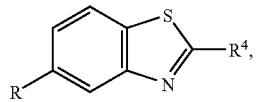
(Ij-1)

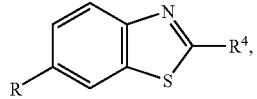
(Ij-2)

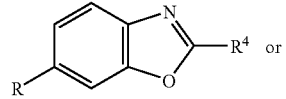
(In-1)

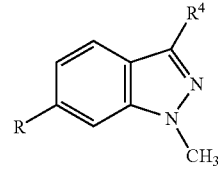
(Ip-1)

wherein $R^4$ denotes H, $C_{1-3}$-alkyl, benzyl, $C_{1-3}$-alkyl-carbonyl, morpholin-4-yl-methyl-carbonyl, $C_{1-2}$-alkoxy-carbonyl, phenylcarbonyl, 5-chloro-1H-indol-2-yl-carbonyl, aminocarbonyl, $C_{1-3}$-alkyl-aminocarbonyl, di-($C_{1-3}$-alkyl)-aminocarbonyl, cyclopropyl-aminocarbonyl, pyrrolidin-1-yl-carbonyl, 3-hydroxy-pyrrolidin-1-yl-carbonyl, piperidin-1-yl-carbonyl, morpholin-4-yl-carbonyl, piperazin-1-yl-carbonyl, N,N-dimethyl-amino-ethyl-amino-carbonyl, phenylamino-carbonyl, pyridinylamino-carbonyl, benzyl-sulphonyl or phenyl-sulphonyl.

Most particularly preferred are those compounds of the above general formula I wherein R denotes a group of the above-mentioned formula, wherein $R^1$ denotes H, tert.-butyl-carbonyl-oxy-methyl or iso-propyloxy-carbonyl-oxy-methyl, $R^2$ and $R^3$ independently of one another represent chlorine, bromine or methyl and A denotes CH, and the heterocyclic group

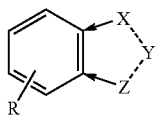

denotes a group of formula

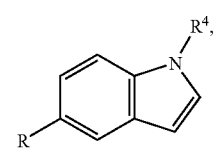 (Ia-1)

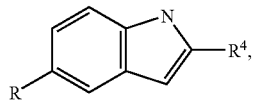 (Ic-1)

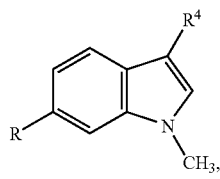 (Id-1)

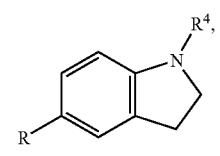 (If-1)

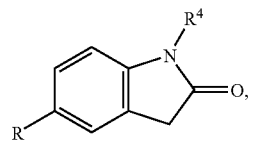 (Ig-1)

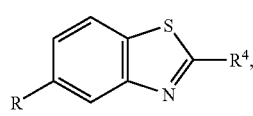 (Ij-1)

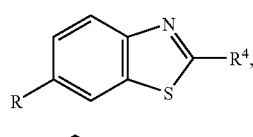 (Ij-2)

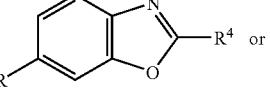 (In-1)

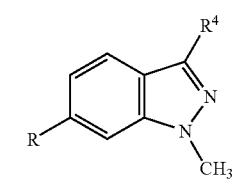 or (Ip-1)

wherein $R^4$ denotes H, $C_{1-2}$-alkyl, benzyl, $C_{1-2}$-alkyl-carbonyl, morpholin-4-yl-methyl-carbonyl, ethoxycarbonyl, phenylcarbonyl, 5-chloro-1H-indol-2-yl-carbonyl, aminocarbonyl, $C_{1-2}$-alkyl-aminocarbonyl, di-($C_{1-2}$-alkyl)-aminocarbonyl, cyclopropyl-aminocarbonyl, pyrrolidin-1-yl-carbonyl, 3-hydroxy-pyrrolidin-1-yl-carbonyl, piperidin-1-yl-carbonyl, morpholin-4-yl-carbonyl, piperazin-1-yl-carbonyl, N,N-dimethyl-amino-ethyl-amino-carbonyl, phenylamino-carbonyl, pyridinylamino-carbonyl, benzyl-sulphonyl or phenyl-sulphonyl, but particularly those compounds of the above general formula I, wherein R denotes a group of the above-mentioned formula, wherein $R^1$ denotes H, tert.-butyl-carbonyl-oxy-methyl or iso-propyloxy-carbonyl-oxy-methyl, $R^2$ and $R^3$ independently of one another denote chlorine or methyl and A denotes CH, and the heterocyclic group

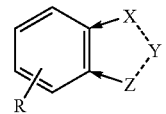

denotes a group of formula

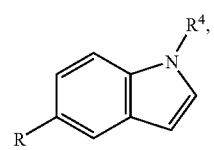 (Ia-1)

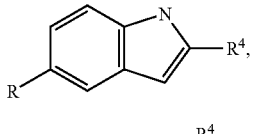 (Ic-1)

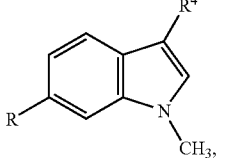 (Id-1)

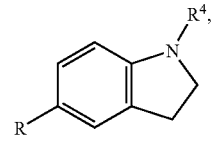 (If-1)

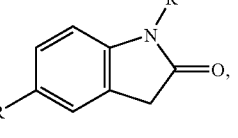 (Ig-1)

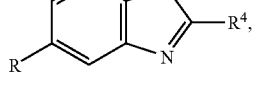 (Ij-1)

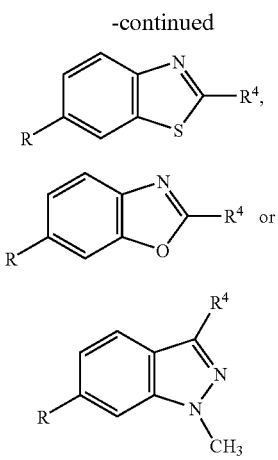

wherein
R[4] denotes H, $C_{1-2}$-alkyl, $C_{1-2}$-alkyl-carbonyl, morpholin-4-yl-methyl-carbonyl, ethoxycarbonyl, 5-chloro-1H-indol-2-yl-carbonyl, aminocarbonyl, $C_{1-2}$-alkyl-aminocarbonyl, di-($C_{1-2}$-alkyl)-aminocarbonyl, pyrrolidin-1-yl-carbonyl, N,N-dimethyl-amino-ethyl-amino-carbonyl or phenylamino-carbonyl, the enantiomers thereof, the mixtures thereof and the salts thereof.

Particular emphasis should be laid on the following compounds of general formula (I):
(1) {[(3,5-dichloro-phenylsulphonyl)-(1-methyl-2-oxo-2,3-dihydro-1H-indol-5-yl)-amino]-methyl}-phosphonic acid,
(2) {[(3,5-dichloro-phenylsulphonyl)-(2-oxo-2,3-dihydro-1H-indol-5-yl)-amino]-methyl}-phosphonic acid,
(3) {[(1-acetyl-2,3-dihydro-1H-indol-5-yl)-(3,5-dichloro-phenylsulphonyl)-amino]-methyl}-phosphonic acid,
(4) {[(3,5-dichloro-phenylsulphonyl)-(1-methylcarbamoyl-2,3-dihydro-1H-indol-5-yl)-amino]-methyl}-phosphonic acid,
(5) 2,2-dimethyl-propionic acid-{[(1-acetyl-2,3-dihydro-1H-indol-5-yl)-(3,5-dichloro-phenylsulphonyl)-amino]-methyl}-(2,2-dimethyl-propionyloxymethoxy)-phosphinoyloxymethyl-ester and
(6) {[(1-acetyl-2,3-dihydro-1H-indol-5-yl)-(3,5-dichloro-phenylsulphonyl)-amino]-methyl}-phosphonic acid-di-isopropoxycarbonyloxymethyl-ester, as well as the enantiomers thereof, the mixtures thereof and the salts thereof.

Some terms used hereinbefore and hereinafter to describe the compounds according to the invention are defined more specifically below.

The term halogen denotes an atom selected from among F, Cl, Br and I, particularly F, Cl and Br.

The term $C_{1-n}$-alkyl, wherein n may have a value as defined hereinbefore or hereinafter, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkyl-carbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbornyl, norcaryl, adamantyl, etc. Preferably the term $C_{3-7}$-cycloalkyl includes saturated monocyclic groups.

The term $C_{3-n}$-cycloalkyloxy or $C_{3-n}$-cycloalkoxy d a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{1-n}$-alkoxy-carbonyl denotes a $C_{1-n}$-alkyl-O—C(=O) group, wherein $C_{1-n}$-alkyl is as hereinbefore defined.

The term $C_{3-n}$-cycloalkyl-carbonyl denotes a $C_{3-n}$-cycloalkyl-C(=O) group, wherein $C_{3-n}$-cycloalkyl is as hereinbefore defined.

The terms $C_{1-n}$-alkyl-amino and di-($C_{1-n}$-alkyl)-amino denote a $C_{1-n}$-alkyl-NH— or a di-($C_{1-n}$-alkyl)-N group, respectively, wherein $C_{1-n}$-alkyl is as hereinbefore defined.

The term $C_{3-n}$-cycloalkyl-amino denotes a $C_{3-n}$-cycloalkyl-NH group, wherein $C_{3-n}$-cycloalkyl is as hereinbefore defined.

The term N—($C_{3-n}$-cycloalkyl)-N—($C_{1-n}$-alkyl)-amino denotes an N—($C_{3-n}$-cycloalkyl)-N—($C_{1-n}$-alkyl)-N group, wherein $C_{3-n}$-cycloalkyl and $C_{1-n}$-alkyl are as hereinbefore defined.

The terms $C_{1-n}$-alkyl-aminocarbonyl and di-($C_{1-n}$-alkyl)-aminocarbonyl denote a $C_{1-n}$-alkyl-NH—C(=O)— or a di-($C_{1-n}$-alkyl)-N—C(=O) group, respectively, wherein $C_{1-n}$-alkyl is as hereinbefore defined.

The term $C_{3-n}$-cycloalkyl-aminocarbonyl denotes a $C_{3-n}$-cycloalkyl-NH—C(=O) group, wherein $C_{3-n}$-cycloalkyl is as hereinbefore defined.

The term N—($C_{3-n}$-cycloalkyl)-N—($C_{1-n}$-alkyl)-amino denotes an N—($C_{3-n}$-cycloalkyl)-N—($C_{1-n}$-alkyl)-N—C(=O) group, wherein $C_{3-n}$-cycloalkyl and $C_{1-n}$-alkyl are as hereinbefore defined.

The terms di-($C_{1-n}$-alkyl)amino and di-($C_{1-n}$-alkyl)aminocarbonyl, wherein n has a value as defined hereinbefore, encompass amino groups which have the same or two different alkyl groups.

The term $C_{1-n}$-perfluoroalkyl denotes a F—(CF2)$_n$ group. Examples of such groups include trifluoromethyl, pentafluoroethyl, heptafluoro-n-propyl, heptafluoro-iso-propyl etc., but preferably trifluoromethyl, pentafluoroethyl.

The term $C_{1-n}$-perfluoroalkoxy denotes a F—(CF2)$_n$—O group. Examples of such groups include trifluoromethoxy, pentafluoroethoxy, heptafluoro-n-propoxy, heptafluoro-iso-propoxy etc., but preferably trifluoromethoxy, pentafluoroethoxy.

The term $C_{1-n}$-alkylsulphonyl denotes a $C_{1-n}$-alkyl-S(=O)$_2$ group, wherein $C_{1-n}$-alkyl is as hereinbefore defined.

The compounds according to the invention may be obtained using methods of synthesis that are known in principle. Preferably the compounds are obtained by methods of preparation that are described more fully hereinafter.

Compounds of general formula I may be prepared according to Method a) shown in Scheme 1, wherein X, Y, Z, $R^1$, $R^2$, $R^3$ and A are as hereinbefore defined, starting from a compound of general formula II.

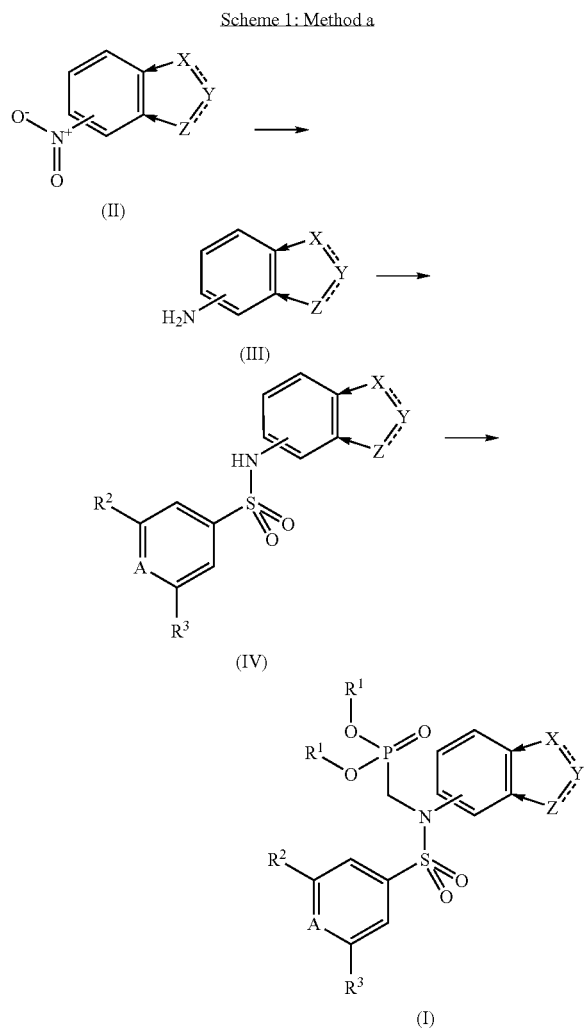

a) Here, compounds of general formula III are obtained by reacting a compound of general formula II with a reducing agent. The starting compounds of general formula II or III are either commercially obtainable or may be prepared by synthesising the heterocyclic group and/or nitrogenation (Houben-Weyl, *Methoden der organischen Chemie*, Volume X/1, 463-890) using methods known per se starting from commercially obtainable compounds.

A suitable reducing agent is for example hydrogen in the presence of a catalyst, such as palladium on charcoal, palladium hydroxide on charcoal or Raney nickel, while palladium on charcoal is particularly suitable. The hydrogenation is carried out in a suitable solvent such as methanol, ethanol, isopropanol, tetrahydrofuran, dichloromethane or ethyl acetate, but preferably methanol, ethanol or tetrahydrofuran, at a pressure between 0.5 and 7 bar, but preferably at a pressure between 0.5 and 3 bar, and at a temperature between 0° C. and 60° C., but preferably at a temperature between 15° C. and 40° C.

Also suitable for the reduction is tin dichloride hydrate in lower alcoholic solvents such as methanol or ethanol at a temperature between ambient temperature and 80° C.

Alternatively titanium trichloride may be used as reducing agent. Suitable solvents are mixtures of acetone and water. The reaction is carried out between 0° C. and 60° C., but preferably between 15° C. and 40° C. and in the presence of ammonium acetate.

Compounds of general formula IV are obtained by sulphonylation of compounds of general formula III.

The sulphonylation is carried out with aromatic sulphonyl chlorides in the presence of a base, such as triethylamine, N,N-diisopropyl-N-ethyl-amine, pyridine, or 4-dimethylamino-pyridine, but preferably pyridine. The reaction may be carried out in suitable solvents, such as diethyl ether, tetrahydrofuran, toluene, pyridine, dichloromethane, or chloroform, but preferably dichloromethane. The temperature may be between 0° C. and 60° C., but preferably between 15° C. and 40° C.

Compounds of general formula I are obtained from compounds of general formula IV by alkylation.

Suitable alkylating agents are methylphosphonic acid ester derivatives that contain at the methyl group a leaving group such as chlorine, bromine, iodine, p-tolylsulphonate, methylsulphonate or trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, and a temperature between 0° C. and 100° C., but preferably between 15° C. and 50° C.

If methyl phosphonate derivatives with ethyl phosphonate groups are used as alkylating agents, compounds of general formula I are obtained wherein $R^1$=ethyl. The ethyl groups therein are preferably cleaved by treating with trimethylsilyl-bromide or trimethylsilyl iodide in dichloromethane or 1,2-dichloroethane.

b) Compounds of general formula VI wherein $R^4$ is bound to X and X denotes nitrogen may for example be obtained by process b) shown in Scheme 2 from compounds of general formula V, wherein —Y . . . Z→ denotes —CH═CH→ or —CH$_2$—CH$_2$—→, while the carbon atoms therein may be substituted as hereinbefore defined and $R^4$ denotes an acyl, sulphonyl, alkoxy-carbonyl, substituted amino-carbonyl or optionally substituted alkyl group and $R^5$ denotes the group R as hereinbefore defined, a nitro group or a group of formula

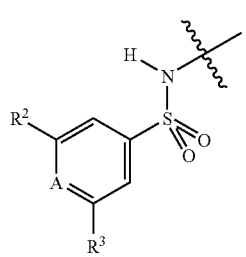

while R, $R^2$, $R^3$ and A are as hereinbefore defined.

Scheme 2: Method b

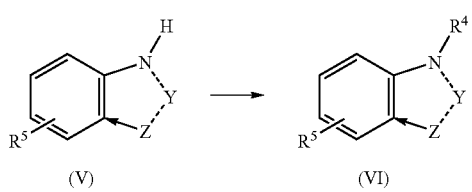

Acyl groups may be introduced by reacting a compound of general formula V with an acylating reagent such as for example an acid chloride or acid anhydride. The reaction may be carried out in the presence of a base such as sodium hydroxide, sodium hydride, sodium carbonate, potassium carbonate, caesium carbonate, triethylamine or N,N-diisopropyl-N-ethyl-amine as well as in a solvent such as dichloromethane, tetrahydrofuran, dioxane or dimethylformamide at temperatures between –30° C. and 200° C., but preferably between 0° C. and 160° C. Alternatively the reaction may be carried out by acylation with an acid. For this, the acid is activated in situ by the addition of diisopropylcarbodiimide, dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) and reacted in a dipolar aprotic solvent such as for example dimethylformamide, dimethylacetamide, tetrahydrofuran, acetonitrile, N-methylpyrrolidone or dimethylsulphoxide, but preferably in dimethylformamide or N-methylpyrrolidone with a compound of general formula V in the presence of a base such as triethylamine, N,N-diisopropyl-N-ethyl-amine and optionally a catalyst such as 4-N,N-dimethylaminopyridine at temperatures between –20° C. and 80° C., but preferably between 0° C. and 50° C.

Sulphonyl groups may be introduced by reacting with a sulphonyl chloride in the presence of a base such as for example sodium carbonate, potassium carbonate, caesium carbonate, triethylamine or N,N-diisopropyl-N-ethyl-amine, but preferably potassium carbonate, in a solvent such as dichloromethane, tetrahydrofuran, dioxane or dimethylformamide at temperatures between –30° C. and 100° C., but preferably between 0° C. and 60° C.

Alkoxycarbonyl groups may be introduced by reacting with an alkyl chloroformate in the presence of a base such as for example sodium carbonate, potassium carbonate, caesium carbonate, triethylamine or N,N-diisopropyl-N-ethyl-amine, but preferably potassium carbonate, in a solvent such as dichloromethane, tetrahydrofuran, dioxane or dimethylformamide at temperatures between –30° C. and 100° C., but preferably between 0° C. and 60° C. Alternatively, alkoxycarbonyl groups are obtained by reacting a compound of general formula V with phosgene in a solvent such as dichloromethane, tetrahydrofuran or dioxane in the presence of a base such as for example sodium carbonate, potassium carbonate, caesium carbonate, triethylamine or N,N-diisopropyl-N-ethyl-amine, but preferably triethylamine or N,N-diisopropyl-N-ethyl-amine, and subsequently treating with an alcohol at temperatures between –20° C. and 100° C., but preferably between 0° C. and 50° C.

Aminocarbonyl groups may be introduced by reacting with an isocyanate, optionally in the presence of a base such as for example sodium carbonate, potassium carbonate, caesium carbonate, triethylamine or N,N-diisopropyl-N-ethyl-amine in a solvent such as dichloromethane, tetrahydrofuran, dioxane or dimethylformamide at temperatures between –30° C. and 150° C., but preferably between 0° C. and 100° C. Alternatively aminocarbonyl groups are obtained by reacting a compound of general formula V with phosgene in a solvent such as dichloromethane, tetrahydrofuran or dioxane in the presence of a base such as for example sodium hydride, sodium carbonate, potassium carbonate, caesium carbonate, triethylamine or N,N-diisopropyl-N-ethyl-amine, but preferably sodium hydride, triethylamine or N,N-diisopropyl-N-ethyl-amine and subsequently treating with an amine at temperatures between –20° C. and 100° C., but preferably between 0° C. and 50° C.

In order to introduce alkyl groups the compounds of general formula V are reacted with a base such as for example sodium hydride, potassium hydride, sodium amide, lithium diisopropylamide, lithium hexamethyldisilazide, potassium hexamethyldisilazide or sodium hexamethyldisilazide and an alkylating agent. The reaction is carried out in a solvent such as for example tetrahydrofuran, 1,4-dioxane, dimethylformamide, dimethylacetamide, N-methylpyrrolidone or acetonitrile at temperatures between –40° C. and 120° C., but preferably between –10° C. and 100° C.

The compounds of general formula VI thus obtained correspond to intermediates from Scheme 1 and may be converted into the end compounds of general formula I according to Process a).

c) Compounds of general formula VIII, wherein $R^4$ is bound to X and X denotes a carbon atom or CH, may be obtained according to Process c) shown in Scheme 3 from compounds of general formula VII wherein ...Y...Z→ denotes =CH—N(H)→, =CH—N(Me)→ or =N—N(Me) →, while the carbon atoms therein may be substituted as hereinbefore defined and $R^4$ denotes an optionally substituted amino-carbonyl or an alkoxy-carbonyl group and $R^6$ denotes nitro or

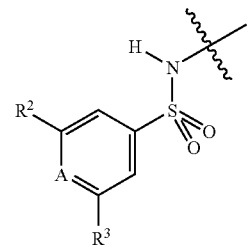

wherein $R^2$, $R^3$ and A are as hereinbefore defined.

Scheme 3: Process c

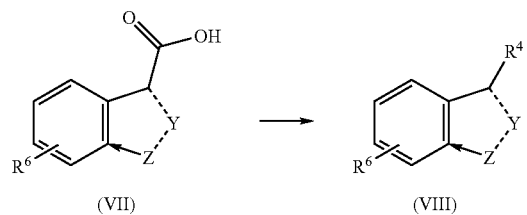

The transformation may be carried out by first converting the acid into an acid chloride. For this, a compound of general formula VII is combined with thionyl chloride, optionally in the presence of a solvent such as toluene or benzene heating it to temperatures between 50° C. and 150° C., but preferably between 80° C. and 120° C. After the elimination of the volatile constituents the acid chloride thus obtained is reacted with the alcohol or amine in a solvent such as dichloromethane, tetrahydrofuran, dioxane or dimethylformamide, but preferably tetrahydrofuran at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine.

Alternatively the acid may be converted into an acid imidazolide. For this a compound of general formula VII is reacted with carbonyldiimidazole in a solvent such as dichloromethane, tetrahydrofuran or dioxane at temperatures between 20° C. and 100° C. The acid imidazolide thus obtained is reacted with the alcohol or amine in a solvent such as dichloromethane, tetrahydrofuran, dioxane or dimethylformamide, but preferably tetrahydrofuran, at temperatures between −30° C. and 150° C., but preferably between 0° C. and 80° C., and optionally in the presence of a base such as triethylamine, N,N-diisopropyl-N-ethyl-amine and optionally in the presence of a catalyst such as 4-N,N-dimethylaminopyridine.

Moreover, compounds of general formula VIII may be prepared by in situ activation of the carboxylic acid. For this, the acid is activated by the addition of diisopropylcarbodiimide, dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) and reacted in a dipolar aprotic solvent such as for example dimethylformamide, dimethylacetamide, tetrahydrofuran, acetonitrile, N-methylpyrrolidone or dimethylsulphoxide, but preferably in dimethylformamide or N-methylpyrrolidone, with an alcohol or an amine in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Compounds of general formula VIII wherein $R^4$ denotes alkoxy-carbonyl may also be prepared by alkylating carboxylic acids of general formula VII. For this, the carboxylic acid is reacted with an alkylating agent. Suitable alkylating agents are alkyl derivatives that contain a leaving group such as chlorine, bromine, iodine, p-tolylsulphonate, methylsulphonate or trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, at a temperature between 0° C. and 100° C., but preferably between 15° C. and 50° C.

The compounds of general formula VIII thus obtained correspond to intermediates from Scheme 1 and may be converted into the end compounds of general formula I according to Process a).

d) Compounds of general formula II, wherein X denotes the group $—C(R^4)=$, where $R^4$ denotes one of the abovementioned optionally substituted alkylcarbonyl or arylcarbonyl groups, and Y and Z are as hereinbefore defined, may be obtained according to Process d) from compounds of general formula II, wherein C denotes the group $—CH=$ and Y and Z are as hereinbefore defined.

To do this, a compound of general formula II, wherein C denotes the group $—CH=$ and Y and Z are as hereinbefore defined, is reacted with an acid chloride or an acid anhydride, but preferably an acid anhydride. The reaction may be carried out without a solvent or with a solvent such as for example dichloromethane, 1,2-dichloroethane, toluene, tetrahydrofuran, 1,4-dioxane, dimethylformamide, dimethylacetamide, N-methyl-pyrrolidone and optionally in the presence of a catalyst such as for example aluminium trichloride or boron trifluoride-etherate and at temperatures between −10° C. and 180° C., but preferably between 0° C. and 120° C.

The compounds of general formula II thus obtained correspond to intermediates from Scheme 1 and may be converted into the end compounds of general formula I according to Process a).

e) Compounds of general formula II, wherein X denotes the group $—C(R^4)=$, where $R^4$ denotes one of the abovementioned optionally substituted aminocarbonyl or alkoxycarbonyl groups, and Y and Z are as hereinbefore defined, may be obtained according to Process e) from compounds of general formula II, wherein X denotes the group $—C(CF_3)=$ and Y and Z are as hereinbefore defined.

The compounds of general formula II, wherein X denotes the group $—C(CF_3)=$ and Y and Z are as hereinbefore defined, may be reacted with 5 to 50%, but preferably 40% sodium or potassium hydroxide solution at temperatures between 0° C. and 200° C., but preferably between ambient temperature and 150° C.

The carboxylic acids of general formula II thus obtained, wherein X denotes the group $—C(COOH)—$, may then be converted into an acid chloride, for example. To do this, the carboxylic acid obtained from the first step of the process is combined with thionyl chloride, optionally in the presence of a solvent such as toluene or benzene and heated to temperatures between 50° C. and 150° C., but preferably between 80° C. and 120° C. After elimination of the volatile constituents the acid chloride thus obtained is reacted with the alcohol or amine in a solvent such as dichloromethane, tetrahydrofuran, dioxane or dimethylformamide, but preferably tetrahydrofuran, at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine.

Alternatively the acid may be converted into an acid imidazolide. For this the carboxylic acid is reacted with carbonyldiimidazole in a solvent such as dichloromethane, tetrahydrofuran or dioxane at temperatures between 20° C. and 100° C. The acid imidazolide thus obtained is reacted with the alcohol or amine in a solvent such as dichloromethane, tetrahydrofuran, dioxane or dimethylformamide, but preferably tetrahydrofuran, at temperatures between −30° C. and 150° C., but preferably between 0° C. and 80° C., and optionally in the presence of a base such as triethylamine, N,N-diisopropyl-N-ethylamine and optionally in the presence of a catalyst such as 4-N,N-dimethylaminopyridine. Moreover, compounds of general formula II, wherein X denotes the group $—C(R^4)=$, where $R^4$ denotes one of the above-mentioned optionally substituted aminocarbonyl or alkoxycarbonyl group, and Y and Z are as hereinbefore defined, may be prepared by in situ activation of the carboxylic acid. For this, the acid is activated by the addition of diisopropylcarbodiimide, dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) and reacted in a dipolar aprotic solvent such as for example dimethylformamide, dimethylacetamide, tetrahydrofuran, acetonitrile, N-methylpyrrolidone or dimethylsulphoxide, but preferably in dimethylformamide or N-methylpyrrolidone, with an alcohol or an amine in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Compounds of general formula II wherein, wherein Y and Z are as hereinbefore defined and X denotes the group —C($R^4$)=, while $R^4$ denotes alkoxy-carbonyl, may be prepared by alkylation of carboxylic acids of general formula VII. To do this the carboxylic acid is reacted with an alkylating agent. Suitable alkylating agents are alkyl derivatives that contain a leaving group such as chlorine, bromine, iodine, p-tolylsulphonate, methylsulphonate or trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, and at a temperature between 0° C. and 100° C., but preferably between 15° C. and 50° C.

The compounds of general formula II thus obtained correspond to intermediates from Scheme 1 and may be converted into the end compounds of general formula I according to Process a).

f) Compounds of general formula I, wherein $R^1$ denotes $C_{1-6}$-alkyl-carbonyl-oxy-$C_{1-3}$-alkyl or $C_{1-6}$-alkoxy-carbonyl-oxy-$C_{1-3}$-alkyl and $R^2$, $R^3$, A, X, Y and Z are as hereinbefore defined, may be obtained according to Process f) starting from compounds of general formula I, wherein $R^1$ denotes hydrogen and $R^2$, $R^3$, A, X, Y and Z are as hereinbefore defined.

Compounds of general formula (I), wherein $R^1$ denotes hydrogen and $R^2$, $R^3$, A, X, Y and Z are as hereinbefore defined, are reacted with $C_{1-6}$-alkyl-carbonyl-oxy-$C_{1-3}$-alkyl-chlorides or $C_{1-6}$-alkoxy-carbonyl-oxy-$C_{1-3}$-alkyl-chlorides. The reaction is carried out in the presence of silver carbonate and catalytic amounts of potassium iodide in a dipolar aprotic solvent such as dimethylformamide, N-methyl-pyrrolidine, acetonitrile, but preferably acetonitrile, optionally with the addition of small amounts of water at temperatures between 0° C. and 150° C., but preferably between ambient temperature and 90° C.

Cyano functionalities may in each case be prepared from primary amides obtained in the syntheses. Suitable methods for this transformation are, for example, reaction with thionyl chloride and optionally catalytic amounts of dimethylformamide in a solvent such as dichloromethane, 1,2-dichloroethane, toluene or acetone at temperatures between 0° C. and 100° C., reaction with trifluoroacetic anhydride or trichloroacetic anhydride, a base such as for example pyridine, triethylamine or N,N-diisopropyl-N-ethyl-amine in a solvent such as for example dichloromethane, 1,2-dichloroethane, tetrahydrofuran, 1,4-dioxane or toluene at temperatures between −10° C. and 100° C., as well as reaction with phosphorus oxychloride and optionally a base such as pyridine or N,N-dimethylaniline in the presence or absence of a solvent such as for example dichloromethane, 1,2-dichloroethane, tetrahydrofuran, 1,4-dioxane or toluene, at temperatures between −10° C. and 120° C.

In the reactions described hereinbefore, any reactive groups present such as carboxy, hydroxy, amino or alkylamino groups may be protected during the reaction by conventional protecting groups which are cleaved again after the reaction.

For example, a protecting group for a carboxy group may be a methyl, ethyl, tert.butyl or benzyl group.

For example, a protecting group for a hydroxy group may be an acetyl, benzyl or tetrahydropyranyl group.

Protecting groups for an amino or alkylamino may be a formyl, acetyl, trifluoroacetyl, ethoxycarbonyl, tert.butoxycarbonyl, benzyloxycarbonyl, benzyl, methoxybenzyl or 2,4-dimethoxybenzyl group.

A carboxymethyl or carboxyethyl unit is cleaved for example by hydrolysis in an aqueous solvent, e.g. in water, methanol/water, isopropanol/water, acetic acid/water, tetrahydrofuran/water or dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

A benzyl, methoxybenzyl or benzyloxycarbonyl group is advantageously cleaved by hydrogenolysis, e.g. with hydrogen in the presence of a catalyst such as palladium on charcoal in a suitable solvent such as methanol, ethanol, ethyl acetate or glacial acetic acid, optionally with the addition of an acid such as hydrochloric acid, at temperatures between 0 and 100° C., but preferably at temperatures between 20 and 60° C., and under a hydrogen pressure of 1 to 7 bar, but preferably 1 to 3 bar. However, a 2,4-dimethoxy-benzyl group is preferably cleaved in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

Moreover, the compounds of general formula I obtained, or intermediate products from the synthesis of compounds of general formula I, as already mentioned hereinbefore, may be resolved into their enantiomers and/or diastereomers. Thus, for example, cis/trans mixtures may be resolved into their cis and trans isomers, and compounds with at least one stereocentre may be resolved into their enantiomers.

Thus, for example, the cis/trans mixtures may be resolved by chromatography into the cis and trans isomers thereof, the compounds of general formula I obtained, or intermediate products from the synthesis of compounds of general formula I, which occur as racemates may be separated by methods known per se (cf. Allinger N. L. and Eliel E. L. in "Topics in Stereochemistry", Vol. 6, Wiley Interscience, 1971) into their optical antipodes and compounds of general formula I, or intermediate products from the synthesis of compounds of general formula I, with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatography on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained, or intermediate products from the synthesis of compounds of general formula I, may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of general formula I obtained, or intermediate products from the synthesis of compounds of general formula I, if they contain a carboxy group, may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formula I are inhibitors of the interaction between human liver glycogen phosphorylase (HLGP) and protein PPP1R3 ($G_L$-subunit of glycogen-associated protein phosphatase 1 (PP1)). The effect of the compounds on the binding of the protein PPP1R3 and the glycogen phosphorylase activated by phosphorylation is determined in a binding test based on SPA technology (Amersham Pharmacia). The binding of the substances inhibits the interaction of the glycogen phosphorylase with the protein PPP1R3B. PII measurements were made in triplicate in the 384-well format (Optiplate, Perkin Elmer).

Human glycogen phosphorylase is recombinantly expressed in *E. coli* and purified. The isolated non-phosphorylated HLGP is radioactively labelled in a marking reaction with phosphorylase kinase (200-500 U/mg, P2014, Sigma) and $^{33}$P-gamma ATP (110 TBq/mmol, Hartmann Analytic) (Ref.: Cohen et al., Methods Enzymol. 1988, Vol 159 pp 390). In a binding test, in a volume of 100 µl (test buffer: 50 mM Tris/HCl pH 7.0, 0.1 mM EGTA, 0.1% mercapto-ethanol), different amounts of a test substance (final concentration: 1 nM to 30 µM) are incubated at ambient temperature for 16 hours with 100000 cpm of labelled HLGP, 375 µg streptavidin-SPA Beads (RPNQ 0007, Amersham Pharmacia), 0.1 µg GL-peptide (Biotin-FPEWPSYLGYEKLGPYY). After centrifuging for 5 minutes at 500 g the plate is measured (Topcount, Packard). The cpm values measured are used to calculate the $IC_{50}$ values specified. The basal value is determined in the absence of the peptide and the maximum value is determined in the absence of the test substance.

The compounds of general formula I have $IC_{50}$ values in the range from 30 nM to 1.3 µM.

In view of their ability to suppress the interaction of glycogen phosphorylase a with the GL-subunit of glycogen-associated protein phosphatase 1 (PP1), the compounds of general formula I according to the invention and the corresponding pharmaceutically acceptable salts thereof are theoretically suitable for treating and/or preventatively treating all those conditions or diseases that can be influenced by inhibiting the interaction of glycogen phosphorylase a with the GL-subunit of glycogen-associated protein phosphatase 1 (PP1). Therefore the compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycemia, hyperinsulinemia, glucose metabolic disorder, insulin resistance, metabolic syndrome, dyslipidemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 0.1 to 1000 mg, preferably 0.5 to 500 mg, by intravenous route, and 1 to 1000 mg, preferably 10 to 500 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include in particular those which potentiate the therapeutic effect of an inhibitor of the interaction of glycogen phosphorylase a with the $G_L$ subunit of glycogen-associated protein phosphatase 1 (PP1) according to the invention with respect to one of the indications mentioned and/or which allow the dosage of an inhibitor of the interaction of glycogen phosphorylase a with the GL subunit of glycogen-associated protein phosphatase 1 (PP1) according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. miglitol, acarbose, voglibose), DPPIV inhibitors (e.g. sitagliptine, vildagliptine), SGLT2-inhibitors, alpha2-antagonists, insulin and insulin analogues, GLP-1 and GLP-1 analogues (e.g. exendin-4) or amylin. Other active substances suitable as combination partners are inhibitors of protein tyrosinephosphatase 1, substances that affect deregulated glucose production in the liver, such as e.g. Inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. P-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the interaction of glycogen phosphorylase a with the $G_L$ subunit of glycogen-associated protein phosphatase 1 (PP1). These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

Example I

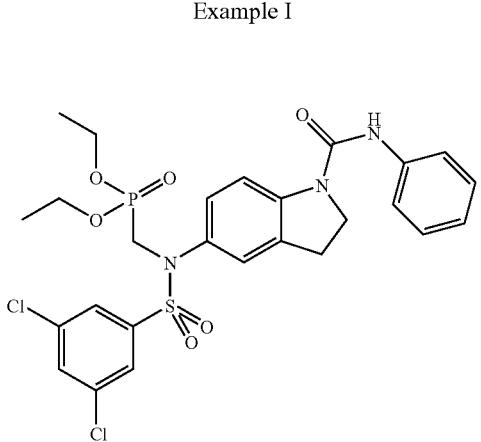

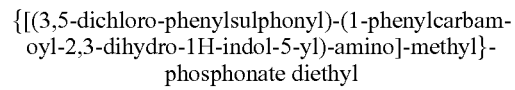

{[(3,5-dichloro-phenylsulphonyl)-(1-phenylcarbamoyl-2,3-dihydro-1H-indol-5-yl)-amino]-methyl}-phosphonate diethyl 1.5 g 5-nitro-2,3-dihydro-1H-indole are dissolved in 12 ml dichloromethane. 510 mg Potassium carbonate and 654 µl phenylisocyanate are added. After stirring for 2 hours the mixture is diluted with ethyl acetate and washed with dilute citric acid solution and saturated sodium chloride solution. After drying with magnesium sulphate the solvents are eliminated in vacuo and the residue is chromatographed on silica gel (cyclohexane/ethyl acetate 30:70 to 0:100).

Yield: 1.05 g (56% of theory)

Mass spectrum (ESI+): m/z=610 [M−H]−

The following compounds are obtained analogously to Example I:

(1) 5-nitro-2,3-dihydro-indole-1-carboxylic acid-phenylamide

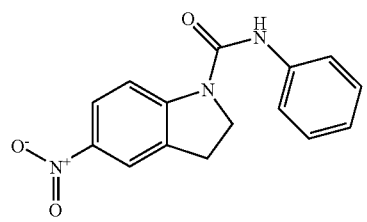

After the reaction the mixture is divided between water and dichloromethane. The solid thus formed is suction filtered and dried in vacuo.

Mass spectrum (ESI+): m/z=284 [M+H]+

Example II

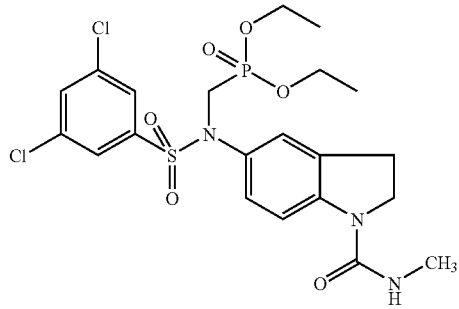

diethyl {[(3,5-dichloro-phenylsulphonyl)-(1-methyl-carbamoyl-2,3-dihydro-1H-indol-5-yl)-amino]-methyl}-phosphonate 1.27 g diethyl {[(3,5-dichloro-phenylsulphonyl)-(2,3-dihydro-1H-indol-5-yl)-amino]-methyl}-phosphonate are dissolved in 10 ml dichloromethane and cooled to 0° C. To this are added 410 µl N,N-diisopropyl-ethylamine and 6.8 ml of a 20% solution of phosgene in toluene. The mixture is left for 1 hour with stirring and then the solvents are eliminated in a nitrogen current. The residue is taken up in 40 ml of tetrahydrofuran, 6.45 ml of a 2 M solution of methylamine in tetrahydrofuran are added and the mixture is stirred overnight at ambient temperature. Then it is diluted with dichloromethane and 1 N hydrochloric acid and washed with semisaturated sodium chloride solution. The organic phase is dried on magnesium sulphate, the solvents are eliminated in vacuo and the residue is purified by chromatography on silica gel (dichloromethane/methanol 95:5 to 60:40).

Yield: 1.21 g (85% of theory)

Mass spectrum (ESI+): m/z=567 [M+NH4]+

The following compounds are obtained analogously to Example II:

(1) ({(3,5-dichloro-phenylsulphonyl)-[1-(2-dimethylamino-ethylcarbamoyl)-2,3-dihydro-1H-indol-5-yl]-amino}-methyl)-phosphonate diethyl

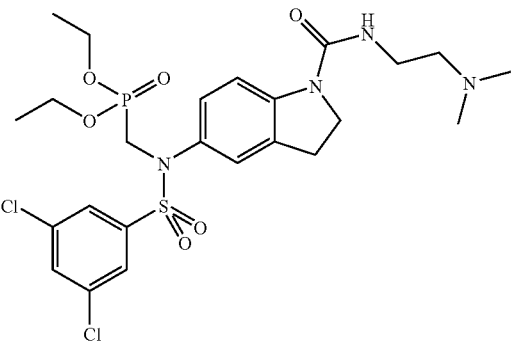

The crude product is further reacted directly in 1 (12).

Mass spectrum (ESI+): m/z=607 [M+H]+

(2) diethyl {[(3,5-dichloro-phenylsulphonyl)-(1-dimethylcarbamoyl-2,3-dihydro-1H-indol-5-yl)-amino]-methyl}-phosphonate

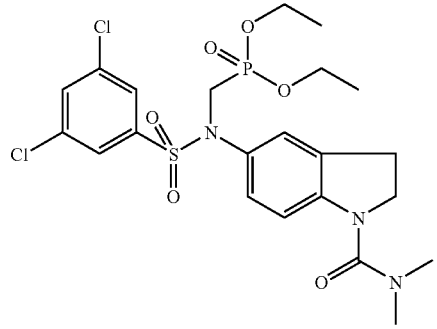

Mass spectrum (ESI+): m/z=564 [M+H]+

(3) 5-nitro-2,3-dihydro-indole-1-carboxylic acid-methylamide

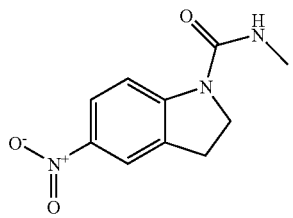

After the reaction has ended the solvents are eliminated in vacuo. The crude product is extracted from 1 N HCl.

Mass spectrum (ESI+): m/z=222 [M+H]+

Example III

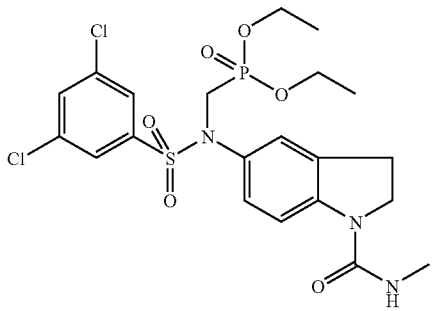

diethyl {[(3,5-dichloro-phenylsulphonyl)-(1-methyl-carbamoyl-2,3-dihydro-1H-indol-5-yl)-amino]-methyl}-phosphonate 2.2 g 5-(3,5-dichloro-phenylsulphonylamino)-2,3-dihydro-indole-1-carboxylic acid-methylamide are dissolved in 15 ml dimethylformamide. To this are added 1.67 g potassium carbonate and 1.32 ml diethoxy-phosphorylmethyl trifluoromethanesulphonate. The mixture is left for 3 hours at ambient temperature with stirring, the solvent is eliminated in vacuo and the residue is divided between water and ethyl acetate. The aqueous phase is extracted twice from ethyl acetate and the combined organic phases are dried on magnesium sulphate. The solvents are eliminated in vacuo and the residue is extracted from diisopropylether/ethyl acetate.

Yield: 2.3 g (76% of theory)

Mass spectrum (ESI+): m/z=550 [M+H]+

The following compounds are obtained analogously to Example III:

(1) tert-butyl 5-[(3,5-dichloro-phenylsulphonyl)-(diethoxy-phosphorylmethyl)-amino]-2,3-dihydro-indole-1-carboxylate

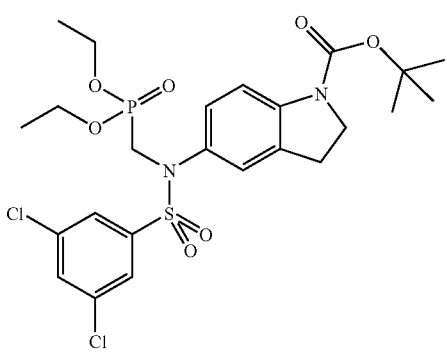

$R_f$ value: 0.27 (silica gel:petroleum ether/ethyl acetate 1:1)

(2) diethyl {[(3,5-dichloro-phenylsulphonyl)-(2-methyl-benzothiazol-5-yl)-amino]-methyl}-phosphonate

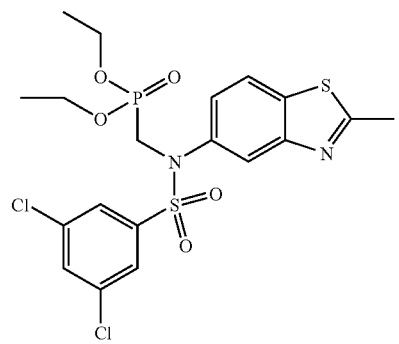

The crude product is chromatographed on silica gel.
Mass spectrum (ESI+): m/z=523 [M+H]+

(3) diethyl {[(3,5-dichloro-phenylsulphonyl)-(2-methyl-benzoxazol-6-yl)-amino]-methyl}-phosphonate

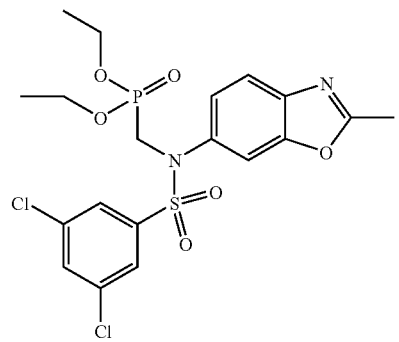

The crude product is chromatographed on silica gel.
Mass spectrum (ESI+): m/z=507 [M+H]+

(4) diethyl {[(3,5-dichloro-phenylsulphonyl)-(1H-indol-5-yl)-amino]-methyl}-phosphonate

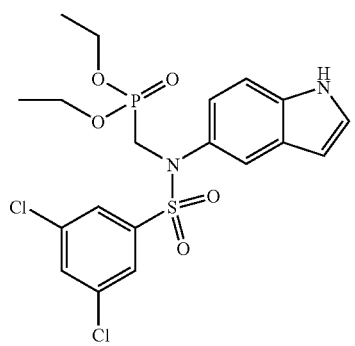

The crude product is chromatographed on silica gel.
Mass spectrum (ESI+): m/z=491 [M+H]+

(5) diethyl {[benzothiazol-6-yl-(3,5-dichloro-phenyl-sulphonyl)-amino]-methyl}-phosphonate

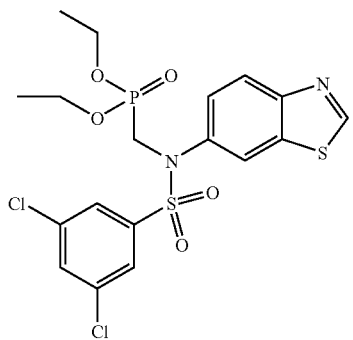

The crude product is chromatographed on silica gel.
Mass spectrum (ESI+): m/z=509 [M+H]+

(6) diethyl {[(3,5-dichloro-phenylsulphonyl)-(1-methyl-2-oxo-2,3-dihydro-1H-indol-5-yl)-amino]-methyl}-phosphonate

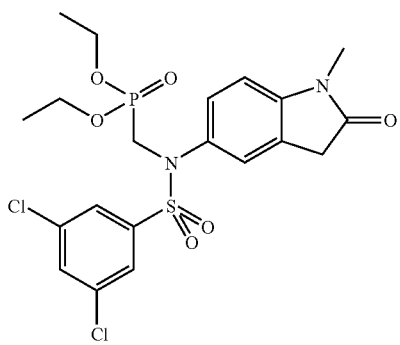

The crude product is chromatographed on silica gel.
Mass spectrum (ESI+): m/z=521 [M+H]+

(7) diethyl {[(3,5-dichloro-phenylsulphonyl)-(2-oxo-2,3-dihydro-1H-indol-5-yl)-amino]-methyl}-phosphonate

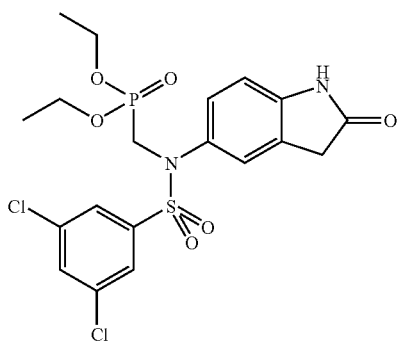

The crude product is chromatographed on silica gel.
Mass spectrum (ESI+): m/z=507 [M+H]+

(8) ethyl 5-[(3,5-dichloro-phenylsulphonyl)-(diethoxy-phosphorylmethyl)-amino]-1H-indole-2-carboxylate

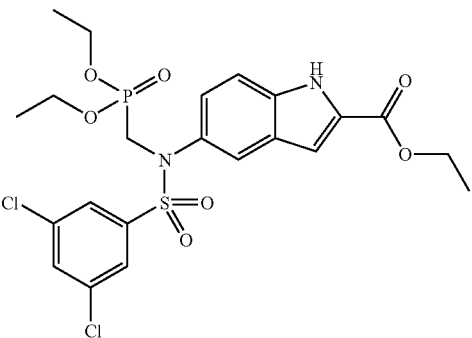

The crude product is chromatographed on silica gel.
Mass spectrum (ESI+): m/z=563 [M+H]+

(9) diethyl {[(3,5-dichloro-phenylsulphonyl)-(1H-indol-6-yl)-amino]-methyl}-phosphonate

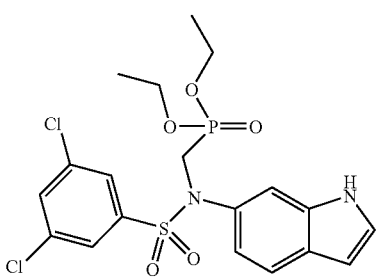

The crude product is chromatographed on silica gel.
Mass spectrum (ESI+): m/z=491 [M+H]+

(10) diethyl {[(3,5-dichloro-phenylsulphonyl)-(2-methyl-benzothiazol-6-yl)-amino]-methyl}-phosphonate

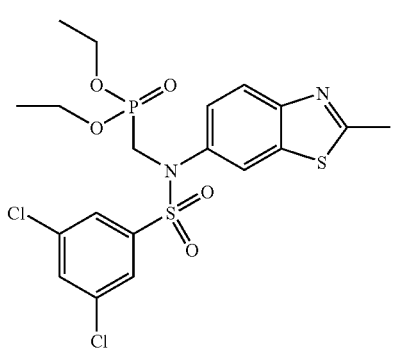

The crude product is chromatographed on silica gel.
Mass spectrum (ESI+): m/z=523 [M+H]+

(11) diethyl {[(3,5-dimethyl-phenylsulphonyl)-(1-methylcarbamoyl-2,3-dihydro-1H-indol-5-yl)-amino]-methyl}-phosphonate

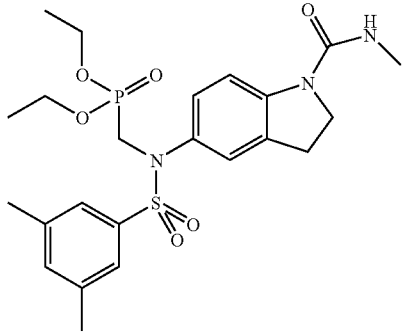

The crude product is chromatographed on silica gel.
Mass spectrum (ESI+): m/z=510 [M+H]+

(12) diethyl {[(3,5-dichloro-phenylsulphonyl)-(2-dimethylcarbamoyl-1H-indol-5-yl)-amino]-methyl}-phosphonate

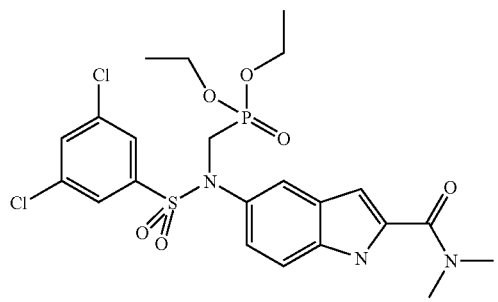

Mass spectrum (ESI+): m/z=562 [M+H]+

(13) diethyl({(3,5-dichloro-phenylsulphonyl)-[1-methyl-3-(pyrrolidine-1-carbonyl)-1H-indol-6-yl]-amino}-methyl)-phosphonate

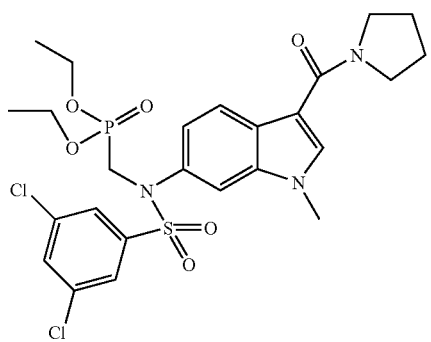

The crude product is chromatographed on silica gel.
Mass spectrum (ESI+): m/z=619 [M+NH4]+

(14) diethyl({(3,5-dichloro-phenylsulphonyl)-[1-methyl-3-(pyrrolidine-1-carbonyl)-1H-indazol-6-yl]-amino}-methyl)-phosphonate

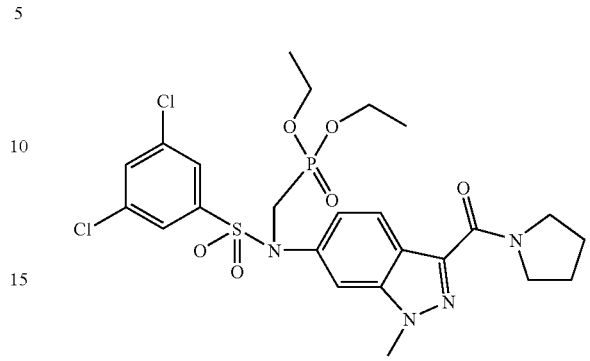

The crude product is chromatographed on silica gel.
Mass spectrum (ESI+): m/z=603 [M+H]+

(15) diethyl {[(3,5-dichloro-phenylsulphonyl)-(1-methyl-3-methylcarbamoyl-1H-indazol-6-yl)-amino]-methyl}-phosphonate

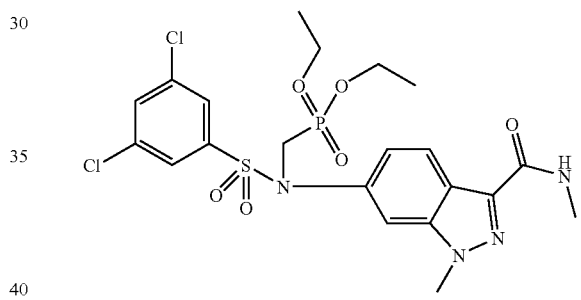

The crude product is chromatographed on silica gel.
Mass spectrum (ESI+): m/z=580 [M+NH4]+

Example IV

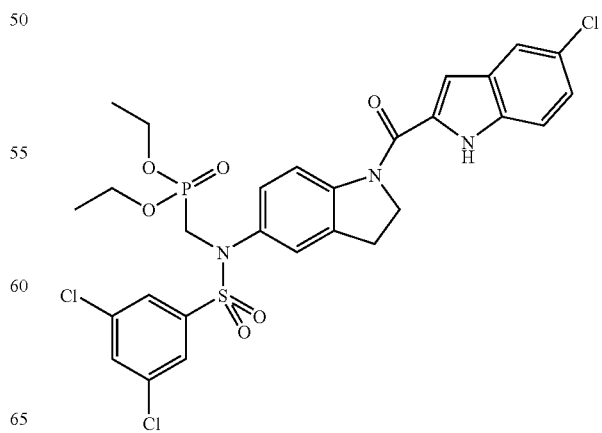

Diethyl {[[1-(5-chloro-1H-indole-2-carbonyl)-2,3-dihydro-1H-indol-5-yl]-(3,5-dichloro-phenylsulphonyl)-amino]-methyl}-phosphonate 50 mg 5-chloro-1H-indole-2-carboxylic acid are dissolved in 2 ml of thionyl chloride and heated to 80° C. for 1 hour. The solvent is eliminated in vacuo and the residue is twice combined with dichloromethane and this is again eliminated in vacuo. The residue is taken up in 5 ml dichloromethane and the solution is added dropwise to a mixture of 100 mg diethyl {[(3,5-dichloro-phenylsulphonyl)-(2,3-dihydro-1H-indol-5-yl)-amino]-methyl}-phosphonate and 60 mg potassium carbonate in 2 ml dimethylformamide. The mixture is stirred for 2 hours at ambient temperature, diluted with ethyl acetate and washed with 1 N HCl and saturated sodium chloride solution. After drying with magnesium sulphate the solvents are eliminated in vacuo and the residue is chromatographed on silica gel (dichloromethane/methanol 95:5 to 70:30).
Yield: 65 mg (48% of theory)
Mass spectrum (ESI+): m/z=670 [M+H]+

Example V

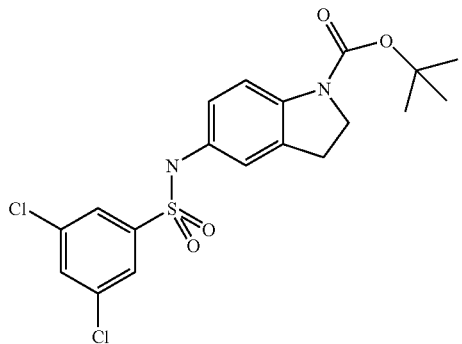

tert-butyl 5-(3,5-dichloro-phenylsulphonylamino)-2,3-dihydro-indole-1-carboxylate 6 g tert-butyl 5-amino-2,3-dihydro-indole-1-carboxylate are dissolved in 50 ml of pyridine and 50 ml dichloromethane. To this is added dropwise a solution of 6.5 g 3,5-dichlorophenylsulphonyl chloride in 50 ml dichloromethane and the mixture is stirred for 1 hour at ambient temperature. Then it is diluted with dichloromethane and washed with 1 N hydrochloric acid and with saturated sodium chloride solution. After drying with magnesium sulphate the solvents are eliminated in vacuo and the residue is chromatographed on silica gel (cyclohexane/ethyl acetate 70:30 to 30:70).
Yield: 8.6 g (76% of theory)
Mass spectrum (ESI+): m/z=460 [M+NH4]+
The following compounds are obtained analogously to Example V:

(1) 3,5-dichloro-N-(2-methyl-benzothiazol-5-yl)-phenylsulphonamide

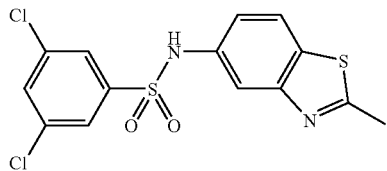

The reaction is carried out in dichloromethane in the presence of 1.4 equivalents of 2,6-lutidine.
Mass spectrum (ESI+): m/z=373 [M+H]+

(2) 3,5-dichloro-N-(2-methyl-benzoxazol-6-yl)-phenylsulphonamide

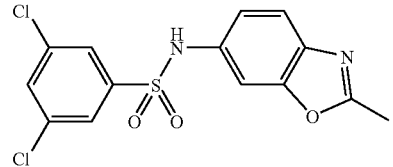

Mass spectrum (ESI+): m/z=357 [M+H]+

(3) 3,5-dichloro-N-(1H-indol-5-yl)-phenylsulphonamide

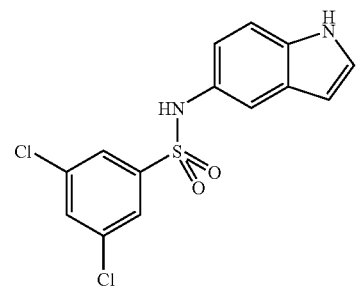

The reaction is carried out in pyridine.
Mass spectrum (ESI+): m/z=339 [M−H]−

(4) N-benzothiazol-6-yl-3,5-dichloro-phenylsulphonamide

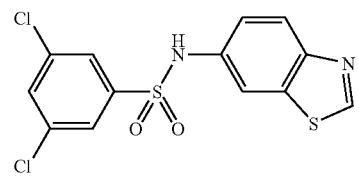

The reaction is carried out in dichloromethane in the presence of 1.4 equivalents of 2,6-lutidine.
Mass spectrum (ESI+): m/z=357 [M−H]−

(5) 3,5-dichloro-N-(1-methyl-2-oxo-2,3-dihydro-1H-indol-5-yl)-phenylsulphonamide

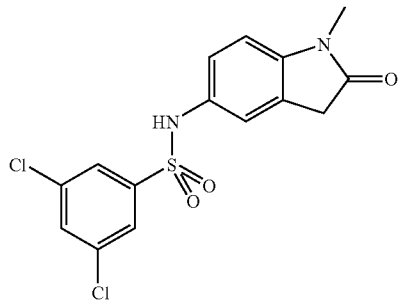

The reaction is carried out in pyridine. The product is extracted from diisopropylether/petroleum ether.
Mass spectrum (ESI+): m/z=371 [M+H]+

(6) 3,5-dichloro-N-(2-oxo-2,3-dihydro-1H-indol-5-yl)-phenylsulphonamide

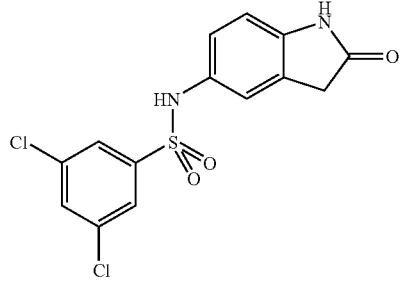

The reaction is carried out in pyridine. The product is extracted from diisopropylether/petroleum ether.
Mass spectrum (ESI+): m/z=355 [M−H]−

(7) ethyl 5-(3,5-dichloro-phenylsulphonylamino)-1H-indole-2-carboxylate

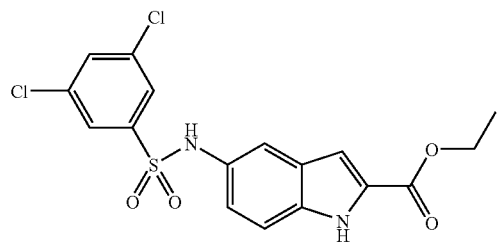

The reaction is carried out in dichloromethane in the presence of 1.4 equivalents of 2,6-lutidine.
Mass spectrum (ESI+): m/z=411 [M−H]−

(8) 3,5-dichloro-N-(1H-indol-6-yl)-phenylsulphonamide

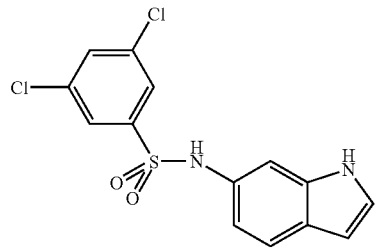

The reaction is carried out in dichloromethane in the presence of 1.4 equivalents of 2,6-lutidine.
Mass spectrum (ESI+): m/z=341 [M+H]+

(9) 5-(3,5-dichloro-phenylsulphonylamino)-2,3-dihydro-indole-1-carboxylic acid-phenylamide

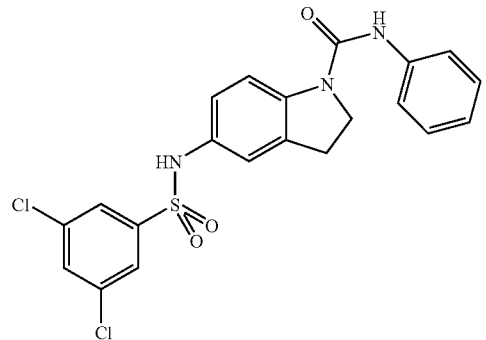

The reaction is carried out in pyridine.
Mass spectrum (ESI+): m/z=462 [M+H]+

(10) 3,5-dichloro-N-(2-methyl-benzothiazol-6-yl)-phenylsulphonamide

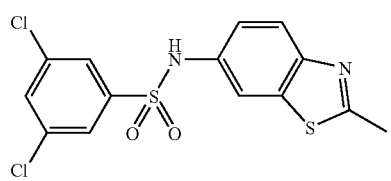

The reaction is carried out in dichloromethane in the presence of 1.4 equivalents of 2,6-lutidine.
Mass spectrum (ESI+): m/z=371 [M−H]−

(11) 5-(3,5-dimethyl-phenylsulphonylamino)-2,3-dihydro-indole-1-carboxylic acid-methylamide

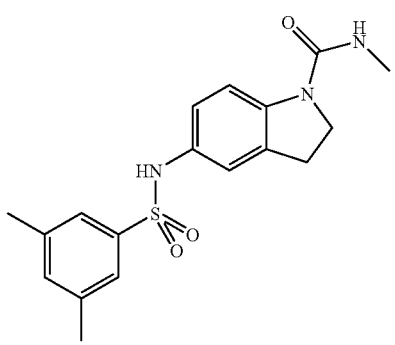

The reaction is carried out in pyridine. The product is extracted from diisopropylether.
Mass spectrum (ESI+): m/z=360 [M+H]+

(12) 5-(3,5-dichloro-phenylsulphonylamino)-2,3-dihydro-indole-1-carboxylic acid-methylamide

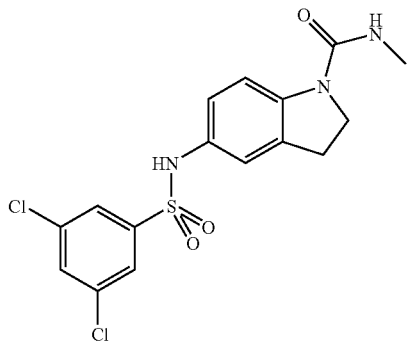

The reaction is carried out in pyridine. The product is extracted from diisopropylether.

Mass spectrum (ESI+): m/z=400 [M+H]+

(13) 3,5-dichloro-N-[1-methyl-3-(pyrrolidine-1-carbonyl)-1H-indol-6-yl]-phenylsulphonamide

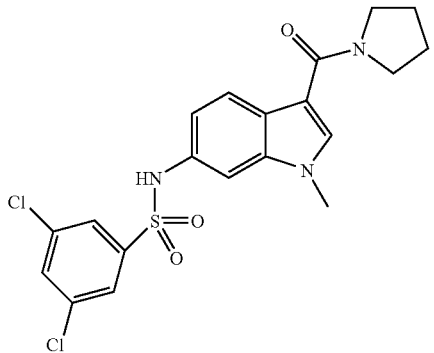

The reaction is carried out in dichloromethane/pyridine 2:1.

Mass spectrum (ESI−): m/z=452 [M+H]+

(14) 3,5-dichloro-N-[1-methyl-3-(pyrrolidine-1-carbonyl)-1H-indazol-6-yl]-phenylsulphonamide

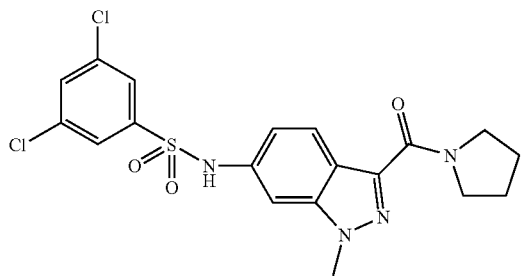

The reaction is carried out in dichloromethane in the presence of 2.3 equivalents pyridine. The product is extracted from a little methanol.

Mass spectrum (ESI−): m/z=453 [M+H]+

(15) 6-(3,5-dichloro-phenylsulphonylamino)-1-methyl-1H-indazole-3-carboxylic acid-methylamide

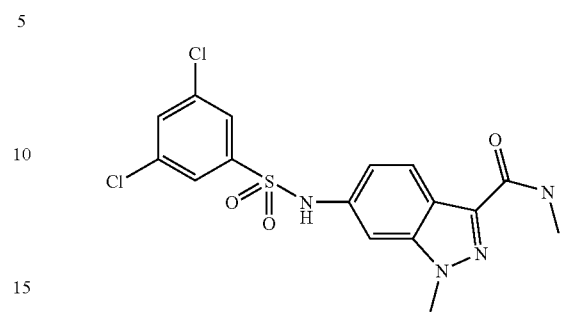

The reaction is carried out in dichloromethane in the presence of 3.8 equivalents pyridine.

Mass spectrum (ESI−): m/z=413 [M+H]+

Example VI

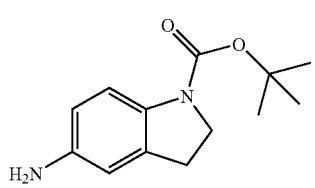

tert-butyl 5-amino-2,3-dihydro-indole-1-carboxylate 6.8 g tert-butyl 5-nitro-2,3-dihydro-indole-1-carboxylate are dissolved in 120 ml of methanol. To this are added 600 mg of palladium on charcoal (10%) and the mixture is hydrogenated for 1.5 hours at ambient temperature. Then the catalyst is filtered off and the solvent is eliminated in vacuo.

Yield: 6 g (100% of theory)

Mass spectrum (ESI+): m/z=235 [M+H]+

The following compounds are obtained analogously to Example VI:

(1) 2-methyl-benzothiazol-5-ylamine

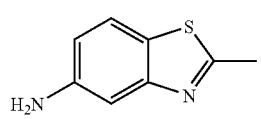

The reaction is carried out in ethyl acetate/methanol 5:1. The product is chromatographed on silica gel.

Mass spectrum (ESI+): m/z=165 [M+H]+

(2) 2-methyl-benzoxazol-6-ylamin

The reaction is carried out in ethyl acetate/methanol 5:1
R_f value: 0.70 (silica gel:ethyl acetate)

(3) 5-amino-1-methyl-1,3-dihydro-indol-2-on

The reaction is carried out in methanol. The crude product is further reacted directly in V (5).

(4) 5-amino-1,3-dihydro-indol-2-on

The reaction is carried out in methanol. The crude product is further reacted directly in V (6).

(5) ethyl 5-amino-1H-indole-2-carboxylate

A 3:2:2 mixture of ethyl acetate, methanol and tetrahydrofuran is used as solvent.
Mass spectrum (ESI+): m/z=205 [M+H]+

(6) 5-amino-2,3-dihydro-indole-1-carboxylic acid-phenylamide

The reaction is carried out in methanol. The crude product is further reacted directly in V (9).

(7) 5-amino-2,3-dihydro-indole-1-carboxylic acid-methylamide

Mass spectrum (ESI+): m/z=192 [M+H]+

(8) (6-amino-1-methyl-1H-indol-3-yl)-pyrrolidin-1-yl-methanone

The reaction is carried out in tetrahydrofuran. The crude product is chromatographed on silica gel.
Mass spectrum (ESI+): m/z=244 [M+H]+

(9) (6-amino-1-methyl-1H-indazol-3-yl)-pyrrolidin-1-yl-methanone

R_f value: 0.40 (silica gel:dichloromethane/methanol 95:5)

(10) 6-amino-1-methyl-1H-indazole-3-carboxylic acid.methylamide

R_f value: 0.40 (silica gel:dichloromethane/methanol 95:5)

Example VII

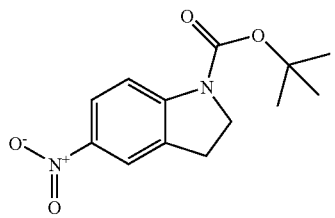

tert-butyl 5-nitro-2,3-dihydro-indole-1-carboxylate 5 g 5-nitro-2,3-dihydro-1H-indole are dissolved in 70 ml acetonitrile. 7.3 g di-tert-butyl-dicarbonate and 900 mg 4-dimethylaminopyridine are added. After stirring for 24 hours at ambient temperature the mixture is divided between 1 N HCl and ethyl acetate. The aqueous phase is extracted with ethyl acetate and the combined organic phases are washed with saturated sodium hydrogen carbonate solution and saturated sodium chloride solution. After drying with magnesium sulphate the solvents are eliminated in vacuo. The residue is extracted from diisopropylether/petroleum ether.

Yield: 6.6 g (82% of theory)

Mass spectrum (ESI+): m/z=265 [M+H]+

Example VIII

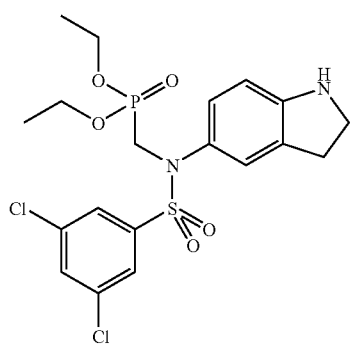

Diethyl {[(3,5-dichloro-phenylsulphonyl-(2,3-dihydro-1H-indol-5-yl)-amino]-methyl}-phosphonate 13.39 g tert-butyl 5-[(3,5-dichloro-phenylsulphonyl)-(diethoxy-phosphorylmethyl)-amino]-2,3-dihydro-indole-1-carboxylate are dissolved in 50 ml dichloromethane. To this are added 10 ml trifluoroacetic acid and the solution is stirred overnight at ambient temperature. The solvents are eliminated in vacuo and the residue is divided between diethyl ether and water. The organic phase is washed with saturated sodium hydrogen carbonate solution and saturated sodium chloride solution. Then magnesium sulphate and activated charcoal are added and the mixture is stirred for 1 hour. After filtration the solvents are eliminated in vacuo.

Yield: 6.3 g (57% of theory)

Mass spectrum (ESI+): m/z=510 [M−NH4]−

Example IX

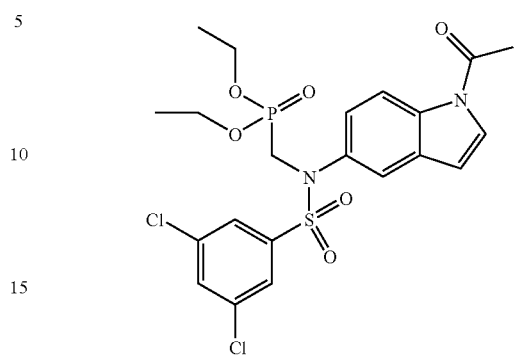

Diethyl {[(1-acetyl-1H-indol-5-yl)-(3,5-dichloro-phenylsulphonyl)-amino]-methyl}-phosphonate 100 mg diethyl {[(3,5-dichloro-phenylsulphonyl)-(1H-indol-5-yl)-amino]-methyl}-phosphonate are dissolved in 1 ml acetic anhydride and refluxed overnight. After cooling to ambient temperature the mixture is divided between ethyl acetate and ice water. Then it is neutralised by the addition of saturated sodium hydrogen carbonate solution. The phases are separated and the organic phase is washed with saturated sodium hydrogen carbonate solution and saturated sodium chloride solution. After drying with magnesium sulphate the solvents are eliminated in vacuo and the residue is chromatographed on silica gel (petroleum ether/ethyl acetate 1:2 to 1:3).

Yield: 78 mg (72% of theory)

Mass spectrum (ESI+): m/z=533 [M+H]+

The following compounds are obtained analogously to Example IX:

(1) diethyl {[[1-(2-chloro-acetyl)-1H-indol-5-yl]-(3,5-dichloro-phenylsulphonyl)-amino]-methyl}-phosphonate

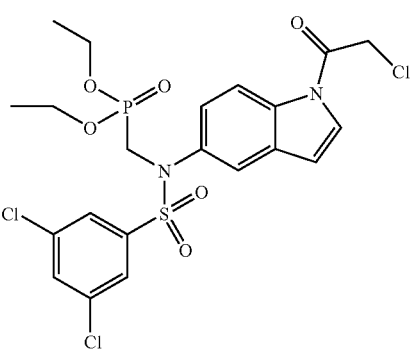

Instead of acetic anhydride, chloroacetic acid anhydride is used.

Mass spectrum (ESI+): m/z=567 [M+H]+

(2) diethyl {[(3-acetyl-1H-indol-6-yl)-(3,5-dichloro-phenylsulphonyl)-amino]-methyl}-phosphonate

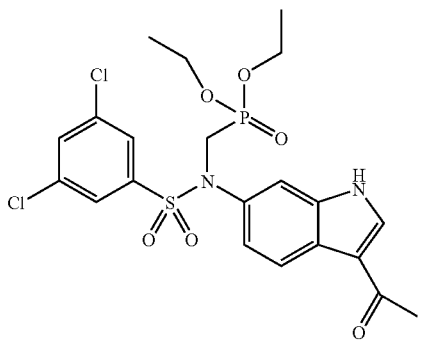

The reaction is carried out at 200° C. for 30 minutes in a sealed vessel in the microwave.
Mass spectrum (ESI+): m/z=531 [M−H]−

Example X

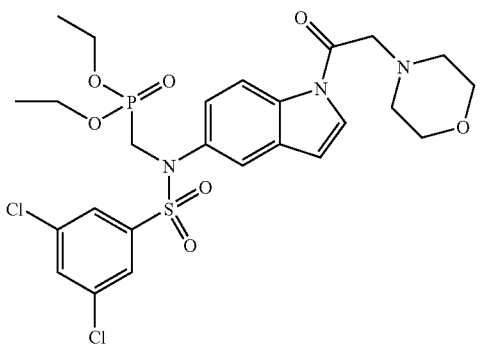

Diethyl({(3,5-dichloro-phenylsulphonyl)-[1-(2-morpholin-4-yl-acetyl)-1H-indol-5-yl]-amino}-methyl)-phosphonate 125 mg diethyl {[[1-(2-chloro-acetyl)-1H-indol-5-yl]-(3,5-dichloro-phenylsulphonyl)-amino]-methyl}-phosphonate are dissolved in 2 ml dimethylformamide, combined with 34 mg potassium carbonate and 22 µl morpholine and stirred overnight at ambient temperature. The mixture is divided between ethyl acetate and water. The organic phase is washed with saturated sodium chloride solution and dried on magnesium sulphate. After drying with magnesium sulphate the solvents are eliminated in vacuo and the residue is chromatographed on silica gel (ethyl acetate/methanol 30:1 to 10:1).
Yield: 76 mg (56% of theory)
Mass spectrum (ESI+): m/z=618 [M+H]+

Example XI

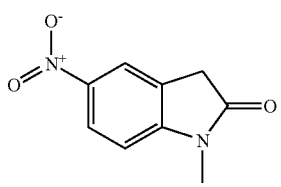

1-methyl-5-nitro-1,3-dihydro-indol-2-one 2 g 1-methyl-1,3-dihydro-indol-2-one are dissolved in 10 ml concentrated sulphuric acid and cooled to 0° C. To this is added dropwise a solution of 620 µl concentrated nitric acid in 2 ml concentrated sulphuric acid and the mixture is stirred for 30 minutes. Then it is poured onto 50 g ice, stirred for 1 hour, the solid is removed by suction filtering and dried in vacuo.
Yield: 1.7 g (65% of theory)
Mass spectrum (ESI+): m/z=193 [M+H]+

Example XII

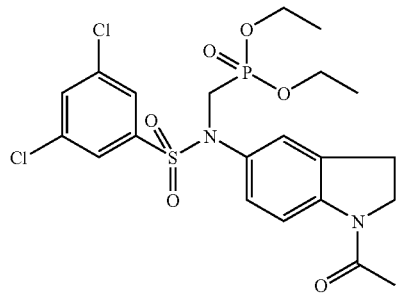

Diethyl {[(1-acetyl-2,3-dihydro-1H-indol-5-yl)-(3,5-dichloro-phenylsulphonyl)-amino]-methyl}-phosphonate 1.45 g diethyl {[(3,5-dichloro-phenylsulphonyl)-(2,3-dihydro-1H-indol-5-yl)-amino]-methyl}-phosphonate are dissolved in 20 ml dichloromethane, combined with 2 ml acetic anhydride and stirred for 2 hours at ambient temperature. The mixture is diluted with dichloromethane, cooled to 0° C. and 20 ml of 4 N sodium hydroxide solution are added thereto. After stirring for 30 minutes the phases are separated and the organic phase is washed with saturated sodium chloride solution. Then it is dried on magnesium sulphate, the solvents are eliminated in vacuo and the residue is chromatographed on silica gel (dichloromethane/methanol 95:5 to 75:25).
Yield: 1.46 g (93% of theory)
Mass spectrum (ESI+): m/z=552 [M+NH4]+

Example XIII

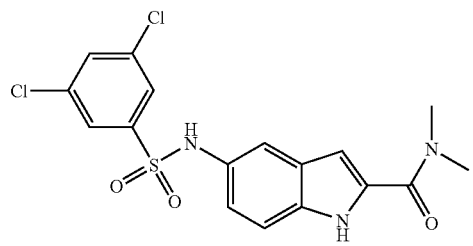

5-(3,5-dichloro-phenylsulphonylamino)-1H-indole-2-carboxylic acid-dimethylamide 110 mg 5-(3,5-dichloro-phenylsulphonylamino)-1H-indole-2-carboxylic acid are dissolved in 4 ml of tetrahydrofuran, combined with 51 mg carbonyldiimidazole and stirred for 3 hours at ambient temperature and for 1 hour at 40° C. After cooling to ambient temperature 600 µl of a 2 M solution of dimethylamine in tetrahydrofuran are added and the mixture is stirred overnight at ambient temperature. The solvent is eliminated in vacuo, the residue is divided between ethyl acetate and 0.5 N hydrochloric acid and the organic phase is washed with water and saturated sodium chloride solution. After drying with magnesium sulphate the solvent is eliminated in vacuo and the residue is chromatographed on silica gel (ethyl acetate).

Yield: 30 mg (26% of theory)
Mass spectrum (ESI+): m/z=410 [M−H]−

Example XIV

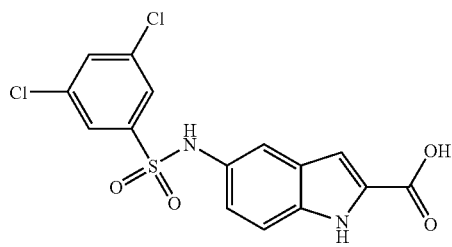

5-(3,5-Dichloro-phenylsulphonylamino)-1H-indole-2-carboxylic acid 100 mg ethyl 5-(3,5-dichloro-phenylsulphonylamino)-1H-indole-2-carboxylate are dissolved in 2 ml of tetrahydrofuran, combined with 2 ml 1 N sodium hydroxide solution and stirred for 48 hours at ambient temperature. Then the tetrahydrofuran is eliminated in vacuo, diluted with some water and combined with 2 ml of 2 N hydrochloric acid. The solid is suction filtered, washed with water and dried in vacuo.

Yield: 60 mg (64% of theory)
Mass spectrum (ESI+): m/z=383 [M−H]−

Example XV

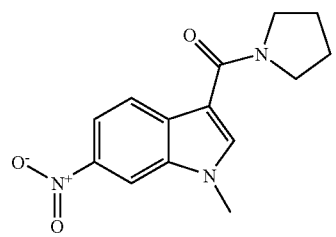

(1-methyl-6-nitro-1H-indol-3-yl)-pyrrolidin-1-yl-methanone 400 mg of 1-methyl-6-nitro-1H-indole-3-carboxylic acid are dissolved in 4 ml dimethylformamide, combined with 774 µl N,N-diisopropyl-N-ethyl-amine as well as 583 mg O-(benzotriazol-1-yl)-N,N,N',N'-tetramethyluronium-tetrafluoroborate (TBTU) and stirred for 45 minutes at ambient temperature. 225 µl of pyrrolidine are added and the mixture is stirred for 5 hours at ambient temperature. Then it is divided between water and ethyl acetate, the organic phase is washed with saturated sodium chloride solution and dried on magnesium sulphate. The solvents are eliminated in vacuo.

Yield: 450 mg (91% of theory)
Mass spectrum (ESI−): m/z=274 [M+H]+

The following compounds are obtained analogously to Example XV:

(1) (1-methyl-6-nitro-1H-indazol-3-yl)-pyrrolidin-1-yl-methanone

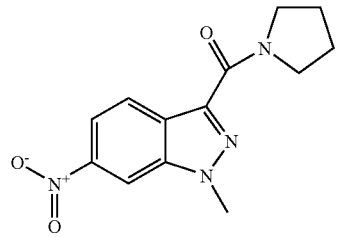

is obtained by reacting a mixture of 1-methyl-6-nitro-1H-indazole-3-carboxylic acid and 2-methyl-6-nitro-2H-indazole-3-carboxylic acid. The product is purified by chromatography on silica gel.
Mass spectrum (ESI−): m/z=275 [M+H]+

(2) 1-methyl-6-nitro-1H-indazole-3-carboxylic acid-methylamide

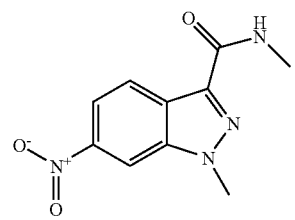

is obtained by reacting a mixture of 1-methyl-6-nitro-1H-indazole-3-carboxylic acid and 2-methyl-6-nitro-2H-indazole-3-carboxylic acid. The product is purified by chromatography on silica gel.
Mass spectrum (ESI−): m/z=235 [M+H]+

Example XVI

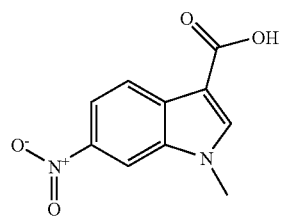

1-methyl-6-nitro-1H-indole-3-carboxylic acid 1.87 g of 2,2,2-trifluoro-1-(1-methyl-6-nitro-1H-indol-3-yl)-ethanone are combined with 32 ml of 6 N sodium hydroxide solution and refluxed for 3 hours. After cooling to ambient temperature the mixture is diluted with water and washed with ethyl acetate. Then by careful addition of 3 N hydrochloric acid the mixture is adjusted to pH 2 and extracted twice with ethyl acetate. The combined organic phases are dried on magnesium sulphate and the solvents are eliminated in vacuo.

Yield: 1.12 g (74% of theory)
Mass spectrum (ESI−): m/z=219 [M−H]−

Example XVII

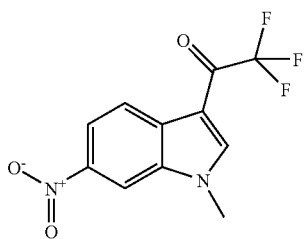

2,2,2-trifluoro-1-(1-methyl-6-nitro-1H-indol-3-yl)-ethanone 2 g 1-methyl-6-nitro-1H-indole are dissolved in 10 ml of tetrahydrofuran and cooled to 0° C. 2.4 ml Trifluoroacetic anhydride are added dropwise to this and the mixture is stirred for 1 hour at 0° C. and for 12 hours at ambient temperature. The solid precipitated is suction filtered and dried.
Yield: 1.87 g (61% of theory)
Mass spectrum (ESI-): m/z=317 [M–HCOO]–

Example XVIII

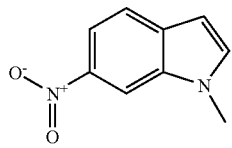

1-methyl-6-nitro-1H-indole 4 g 6-nitro-1H-indole are added batchwise at 0° C. to 800 mg sodium hydride (60% in mineral oil) in 20 mg dimethyl-formamide. The mixture is stirred for 10 minutes, then 1.86 ml methyl iodide are added dropwise and the mixture is left overnight to come up to ambient temperature. Then it is divided between water and ethyl acetate, the aqueous phase is extracted with ethyl acetate and the combined organic phases are washed with saturated sodium chloride solution. After drying with magnesium sulphate the solvents are eliminated in vacuo.
Yield: 4.54 g (104% of theory)
Mass spectrum (ESI⁻): m/z=177 [M+H]⁺

Example IXX

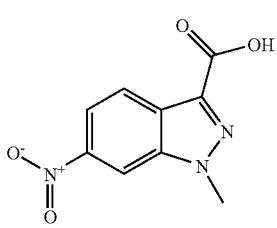

1-methyl-6-nitro-1H-indazole-3-carboxylic acid and

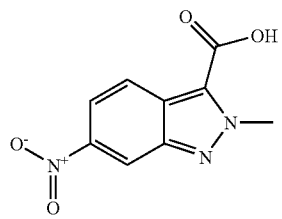

2-methyl-6-nitro-2H-indazole-3-carboxylic acid 670 mg of a mixture of methyl 1-methyl-6-nitro-1H-indazole-3-carboxylate and methyl 2-methyl-6-nitro-2H-indazole-3-carboxylate (Example XX) are dissolved in 20 ml of ethanol, combined with 10 ml 1 M sodium hydroxide solution and stirred for 2 hours. Then 10 ml of 1 M hydrochloric acid are added, the mixture is diluted with water and the precipitated solid is suction filtered. Then the solid is dissolved in dichloromethane/methanol 90:10. After drying with magnesium sulphate the solvents are eliminated in vacuo and the residue is dried in vacuo. 640 mg of a mixture of 1-methyl-6-nitro-1H-indazole-3-carboxylic acid and 2-methyl-6-nitro-2H-indazole-3-carboxylic acid is obtained which is further reacted directly in Example XV (1) or in XV (2), respectively.

Example XX

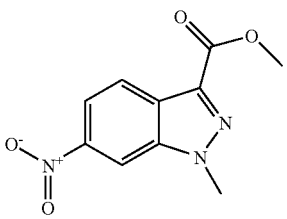

methyl 1-methyl-6-nitro-1H-indazole-3-carboxylate and

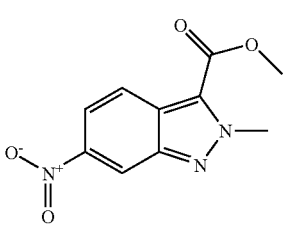

methyl 2-methyl-6-nitro-2H-indazole-3-carboxylate 830 mg 6-nitro-1H-indazole-3-carboxylic acid are dissolved in 16 ml dimethylformamide, combined with 1.66 g potassium carbonate and 823 µl methyl iodide and stirred for 4 hours at 50° C. After cooling to ambient temperature the mixture is divided between water and ethyl acetate. The aqueous phase is extracted twice with ethyl acetate and the combined organic phases are washed with saturated sodium chloride solution. After drying with magnesium sulphate the solvents are eliminated in vacuo. The residue is dissolved in hot dimethylformamide and after cooling to ambient temperature the precipitated solid is suction filtered and washed with diethyl ether. 670 mg of a mixture of methyl 1-methyl-6-nitro-1H-indazole-3-carboxylate and 2 methyl-methyl-6-nitro-2H-indazole-3-carboxylate is obtained, which is further reacted directly in Example IXX.

Example XXI

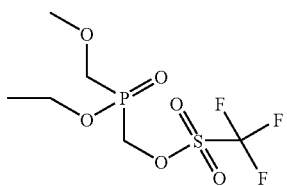

Diethoxy-phosphorylmethyl trifluoro-methanesulphonate 5.01 ml diethyl-(hydroxyethyl)-phosphonate are dissolved in 50 ml dichloromethane, combined with 4.42 ml of 2,6-lutidine and cooled to −50° C. Then a solution of 6 ml trifluoromethanesulphonic acid anhydride in 10 ml dichloromethane is slowly added dropwise. Within 1.5 hours the mixture is allowed to come up to 0° C. and then diluted with 300 ml cold diethyl ether. Any solids precipitated are filtered off and the filtrate is washed twice with ice water, once with 1 N hydrochloric acid and once with saturated sodium chloride solution. After drying with sodium sulphate the solvents are eliminated in vacuo.
Yield: 8.2 g (89% of theory)
Mass spectrum (ESI$^+$): m/z=301 [M+H]$^+$
Preparation of the Final Compounds:

Example 1

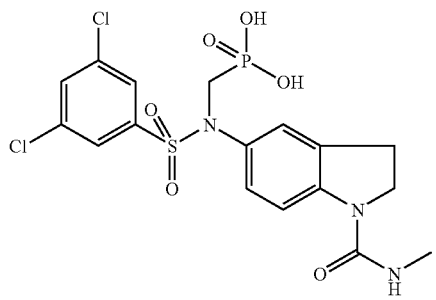

{[(3,5-dichloro-phenylsulphonyl)-(1-methylcarbamoyl-2,3-dihydro-1H-indol-5-yl)-amino]-methyl}-phosphonic acid 1.2 g diethyl {[(3,5-dichloro-phenylsulphonyl)-(1-methyl-carbamoyl-2,3-dihydro-1H-indol-5-yl)-amino]-methyl}-phosphonate are dissolved in 30 ml dichloromethane. 1.2 ml of trimethylsilylbromide are added with stirring. Then the mixture is refluxed for 2 hours and after cooling to ambient temperature combined with 30 ml of methanol. The mixture is stirred for 1 hour, the solvents are eliminated in vacuo, another 30 ml of methanol are added and the mixture is stirred for a further 10 minutes. Then the solvent is eliminated in vacuo and the residue is dried in vacuo at 80° C. Then it is extracted from diethyl ether, the solid is suction filtered and dried in vacuo.
Yield: 990 mg (92% of theory)
Mass spectrum (ESI$^+$): m/z=511 [M+NH4]$_+$ The following compounds are obtained analogously to Example 1:

(1) {[(3,5-dichloro-phenylsulphonyl)-(1-phenylcarbamoyl-2,3-dihydro-1H-indol-5-yl)-amino]-methyl}-phosphonic acid

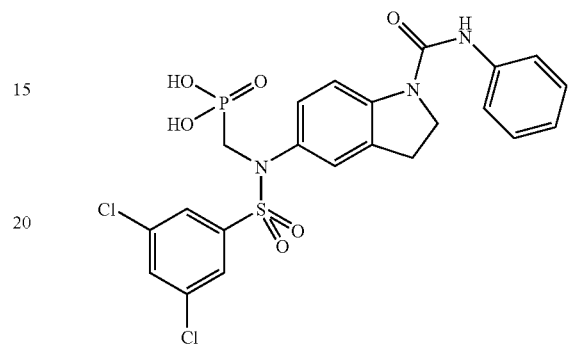

The crude product is extracted from diisopropylether/cyclohexane.
Mass spectrum (ESI+): m/z=554 [M−H]−

(2) {[(3,5-dichloro-phenylsulphonyl)-(2-methyl-benzothiazol-5-yl)-amino]-methyl}-phosphonic acid

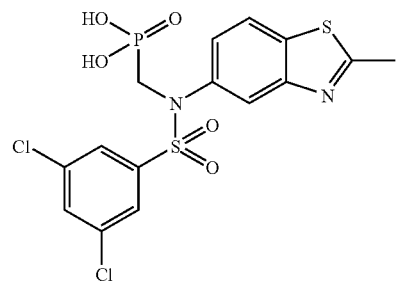

The crude product is extracted from diisopropylether/diethyl ether.
Mass spectrum (ESI+): m/z=467 [M+H]+

(3) {[(3,5-dichloro-phenylsulphonyl)-(2-methyl-benzoxazol-6-yl)-amino]-methyl}-phosphonic acid

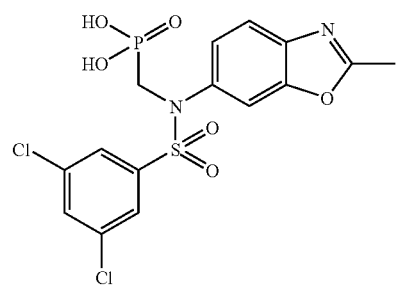

The crude product is extracted from water/ethanol.
$^1$H-NMR (400 MHz, d$_6$-DMSO): 2.59 (s, 3H); 3.64 (d, J=11.2 Hz, 2H); 6.99 (d, J=8.4 Hz, 1H); 7.44-7.58 (m, 4H); 7.92 (s, 1H)

(4) {[(1-acetyl-1H-indol-5-yl)-(3,5-dichloro-phenyl-sulphonyl)-amino]-methyl}-phosphonic acid

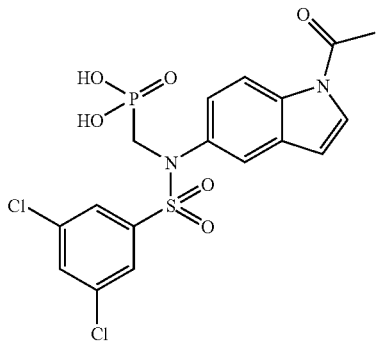

The crude product is extracted from water.
Mass spectrum (ESI+): m/z=477 [M+H]+

(5) {[benzothiazol-6-yl-(3,5-dichloro-phenylsulpho-nyl)-amino]-methyl}-phosphonic acid

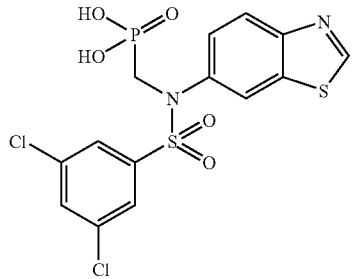

The product is precipitated on stirring with methanol and is suction filtered and dried.
Mass spectrum (ESI+): m/z=453 [M+H]+

(6) ({(3,5-dichloro-phenylsulphonyl)-[1-(2-morpho-lin-4-yl-acetyl)-1H-indol-5-yl]-amino}-methyl)-phosphonic acid.HBr

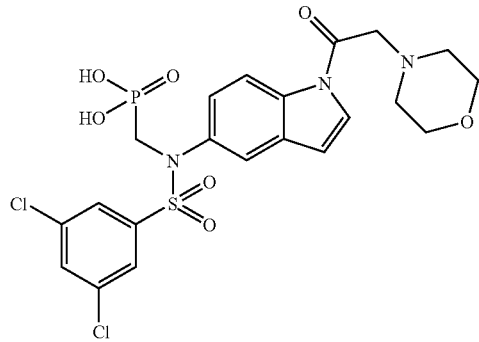

After the first addition of methanol the mixture is stirred for 1 hour and then combined with 11 equivalents of sodium hydrogen carbonate. After 10 minutes some water is added, the mixture is stirred for 5 minutes and then the solvents are eliminated in vacuo. The residue is taken up in dichloromethane/methanol 10:1, the solid is filtered off and the mother liquor is freed from the solvents in vacuo. The residue is triturated from diethyl ether, the solid is suction filtered and dried.
Mass spectrum (ESI+): m/z=562 [M+H]+

(7) {[(3,5-dichloro-phenylsulphonyl)-(1-methyl-2-oxo-2,3-dihydro-1H-indol-5-yl)-amino]-methyl}-phosphonic acid

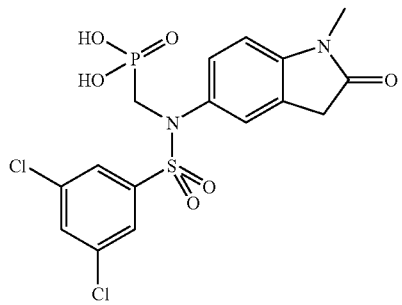

The crude product is extracted from diisopropylether/cyclohexane.
Mass spectrum (ESI+): m/z=463 [M−H]−

(8) {[(3,5-dichloro-phenylsulphonyl)-(2-oxo-2,3-dihydro-1H-indol-5-yl)-amino]-methyl}-phosphonic acid

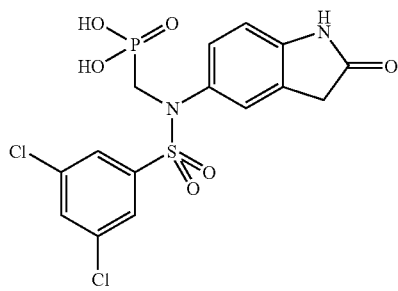

The crude product is extracted from diisopropylether/cyclohexane.
Mass spectrum (ESI+): m/z=449 [M−H]−

(9) ethyl 5-[(3,5-dichloro-phenylsulphonyl)-phosphonomethyl-amino]-1H-indole-2-carboxylate

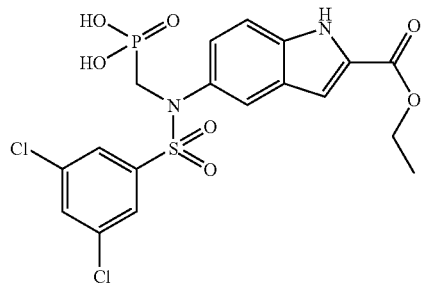

The crude product is extracted from diethyl ether.
$^1$H-NMR (400 MHz, $d_6$-DMSO): 1.34 (t, J=7.2 Hz, 3H); 3.93 (d, J=11.2 Hz, 2H); 4.34 (q, J=7.2 Hz, 2H); 6.97 (dd, J=1.2 Hz and 8.8 Hz, 1H); 7.13 (d, J=1.6 Hz, 1H); 7.35 (d, J=8.8 Hz, 1H); 7.45 (d, J=1.6 Hz, 1H); 7.52 (d, J=1.6 Hz, 2H); 7.99 (t, J=1.6 Hz, 1H); 11.98 (s, 1H)

(10) {[(3-acetyl-1H-indol-6-yl)-(3,5-dichloro-phenylsulphonyl)-amino]-methyl}-phosphonic acid

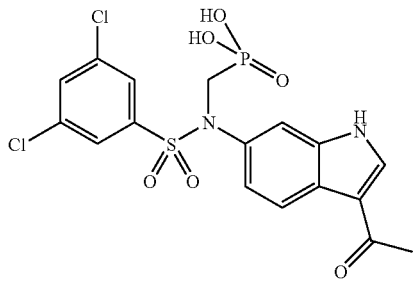

The crude product is extracted from diethyl ether and then from dichloromethane.

Mass spectrum (ESI+): m/z=475 [M−H]−

(11) {[(3,5-dichloro-phenylsulphonyl)-(2,3-dihydro-1H-indol-5-yl)-amino]-methyl}-phosphonic acid.HBr

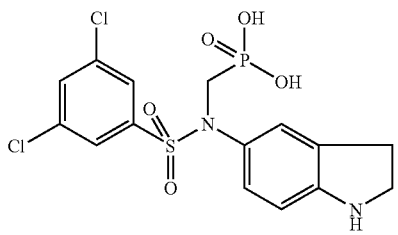

The crude product is dissolved in methanol, diluted with water and then washed with ethyl acetate. The aqueous phase is freeze-dried.

Mass spectrum (ESI+): m/z=435 [M−H]−

(12) ({(3,5-dichloro-phenylsulphonyl)-[1-(2-dimethylamino-ethylcarbamoyl)-2,3-dihydro-1H-indol-5-yl]-amino}-methyl)-phosphonic acid

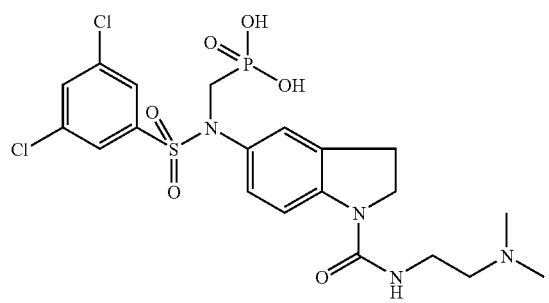

The crude product is dissolved in methanol, diluted with water and then washed with ethyl acetate. The aqueous phase is freeze-dried. The residue is dissolved in methanol and the solvent is eliminated in vacuo. Then the substance is dried in vacuo at 80° C. and the residue thus obtained is extracted from diethyl ether.

Mass spectrum (ESI+): m/z=551 [M+H]+

(13) {[(1-acetyl-2,3-dihydro-1H-indol-5-yl)-(3,5-dichloro-phenylsulphonyl)-amino]-methyl}-phosphonic acid

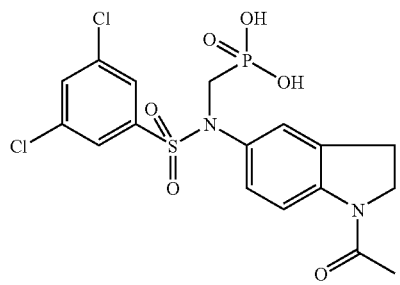

The crude product is extracted from dichloromethane/methanol 95:5. The solvents are largely eliminated in vacuo and then the substance is extracted from ethyl acetate. The solid is suction filtered and dried.

Mass spectrum (ESI+): m/z=496 [M+NH4]+

(14) {[[1-(5-chloro-1H-indole-2-carbonyl)-2,3-dihydro-1H-indol-5-yl]-(3,5-dichloro-phenylsulphonyl)-amino]-methyl}-phosphonic acid

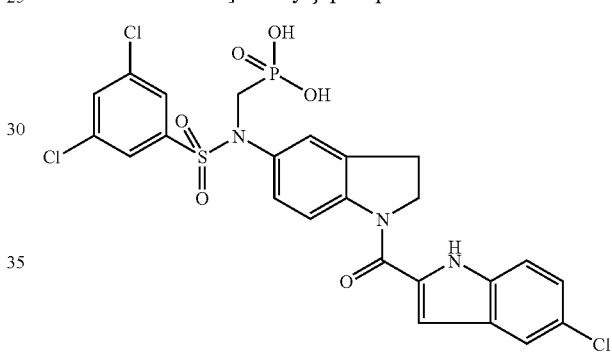

The crude product is extracted from diethyl ether/methanol.

Mass spectrum (ESI+): m/z=612 [M−H]−

(15) {[(3,5-dichloro-phenylsulphonyl)-(1-dimethylcarbamoyl-2,3-dihydro-1H-indol-5-yl)-amino]-methyl}-phosphonic acid

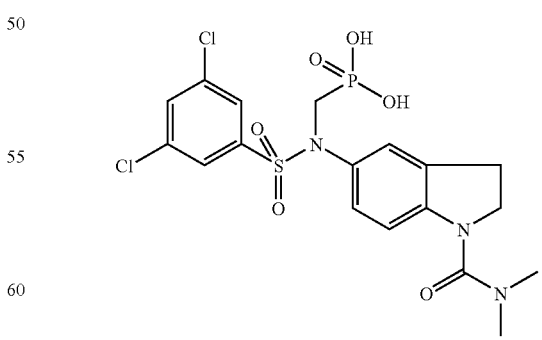

The crude product is extracted from diethyl ether.
$^1$H-NMR (400 MHz, $d_6$-DMSO): 2.83-2.99 (m, 8H); 3.80-3.86 (m, 4H); 6.77-6.85 (m, 2H); 6.95 (s, 1H); 7.53 (d, J=1.6 Hz, 2H); 8.00 (t, J=1.6 Hz, 1H)

(16) {[(3,5-dichloro-phenylsulphonyl)-(2-methyl-benzothiazol-6-yl)-amino]-methyl}-phosphonic acid

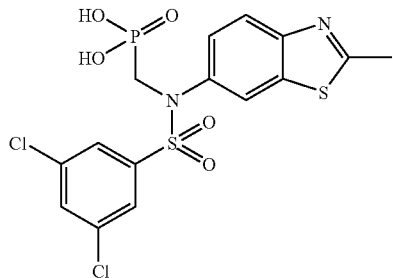

The crude product is extracted from diethyl ether.
$^1$H-NMR (400 MHz, $d_6$-DMSO): 2.79 (s, 3H); 4.00 (d, J=11.2 Hz, 2H), 7.15 (dd, J=2.0 Hz and 8.8 Hz, 1H); 7.55 (d, J=2.0 Hz, 2H); 7.71 (d, J=2.0 Hz, 1H); 7.97 (d, J=8.8 Hz, 1H); 8.01 (t, J=2.0 Hz, 1H)

(17) {[(3,5-dimethyl-phenylsulphonyl)-(1-methylcarbamoyl-2,3-dihydro-1H-indol-5-yl)-amino]-methyl}-phosphonic acid

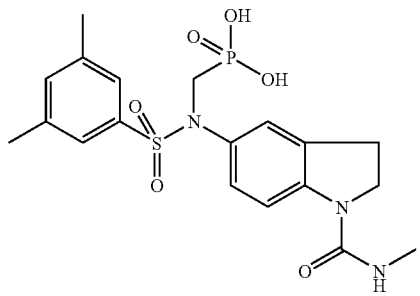

The crude product is extracted from ethanol.
Mass spectrum (ESI+): m/z=471 [M+NH4]+

(18) {[(3,5-dichloro-phenylsulphonyl)-(2-dimethylcarbamoyl-1H-indol-5-yl)-amino]-methyl}-phosphonic acid

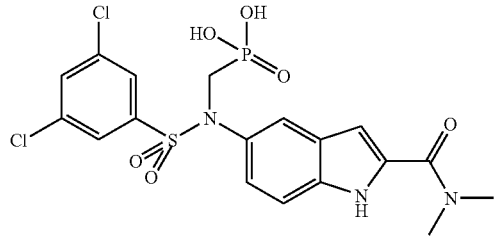

The crude product is extracted from diethyl ether.
Mass spectrum (ESI+): m/z=504 [M−H]−

(19) ({(3,5-dichloro-phenylsulphonyl)-[1-methyl-3-(pyrrolidine-1-carbonyl)-1H-indol-6-yl]-amino}-methyl)-phosphonic acid

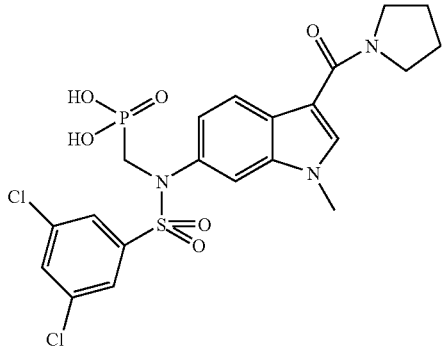

The crude product is extracted from methanol/water.
Mass spectrum (ESI+): m/z=546 [M+H]+

(20) ({(3,5-dichloro-phenylsulphonyl)-[1-methyl-3-(pyrrolidine-1-carbonyl)-1H-indazol-6-yl]-amino}-methyl)-phosphonic acid

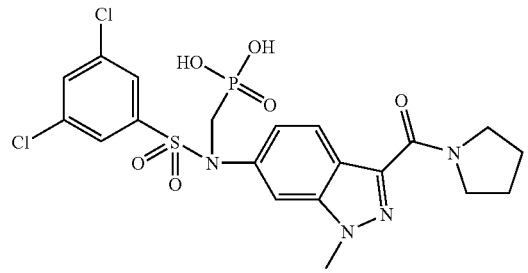

The crude product is extracted from diethyl ether.
Mass spectrum (ESI+): m/z=547 [M+H]+

(21) {[(3,5-dichloro-phenylsulphonyl)-(1-methyl-3-methylcarbamoyl-1H-indazol-6-yl)-amino]-methyl}-phosphonic acid

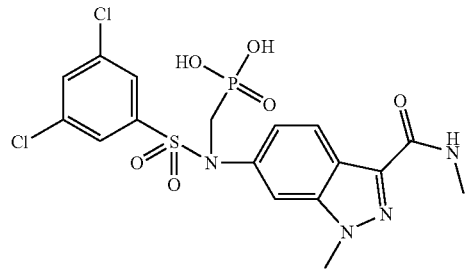

The crude product is extracted from diethyl ether.
Mass spectrum (ESI+): m/z=524 [M+NH4]+

Example 2

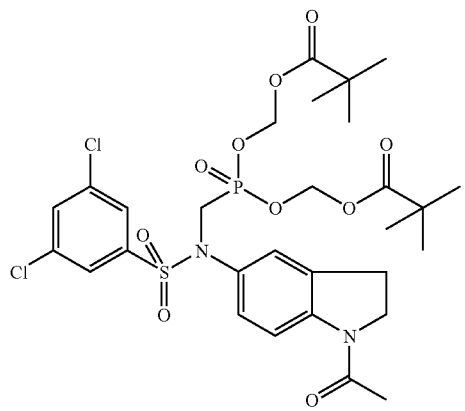

{[(1-acetyl-2,3-dihydro-1H-indol-5-yl)-(3,5-dichloro-phenylsulphonyl)-amino]-methyl}-(2,2-dimethyl-propionyloxymethoxy)-phosphinoyloxymethyl 2,2-dimethyl-propionate 300 mg {[(1-acetyl-2,3-dihydro-1H-indol-5-yl)-(3,5-dichloro-phenylsulphonyl)-amino]-methyl}-phosphonic acid are dissolved in 8 ml acetonitrile, and 400 mg of silver carbonate, 10 mg of potassium iodide and 5 µl of water are added. Then the mixture is heated to 70° C. and 465 µl of chloromethyl pivalate are added. The mixture is stirred for 12 hours, cooled to ambient temperature, diluted with methanol, combined with activated charcoal, filtered and the solvents are eliminated in vacuo. The residue is extracted from diethyl ether. The solid thus obtained is chromatographed on silica gel (dichloromethane/methanol 95:5 to 85:15). The product thus obtained is extracted from diethyl ether/petroleum ether.

Yield: 125 mg (28% of theory)

Mass spectrum (ESI+): m/z=724 [M+NH4]+

The following compounds are obtained analogously to Example 2:

(1) {[(3,5-dichloro-phenylsulphonyl)-(1-methylcarbamoyl-2,3-dihydro-1H-indol-5-yl)-amino]-methyl}-(2,2-dimethyl-propionyloxymethoxy)-phosphinoyloxymethyl 2,2-dimethyl-propionate

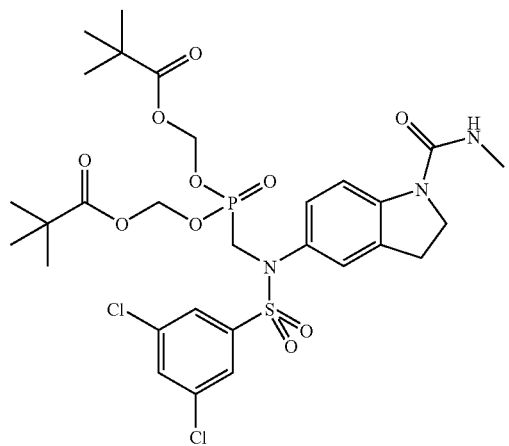

Mass spectrum (ESI+): m/z=739 [M+NH4]+

(2) diisopropoxycarbonyloxymethyl {[(1-acetyl-2,3-dihydro-1H-indol-5-yl)-(3,5-dichloro-phenylsulphonyl)-amino]-methyl}-phosphonate

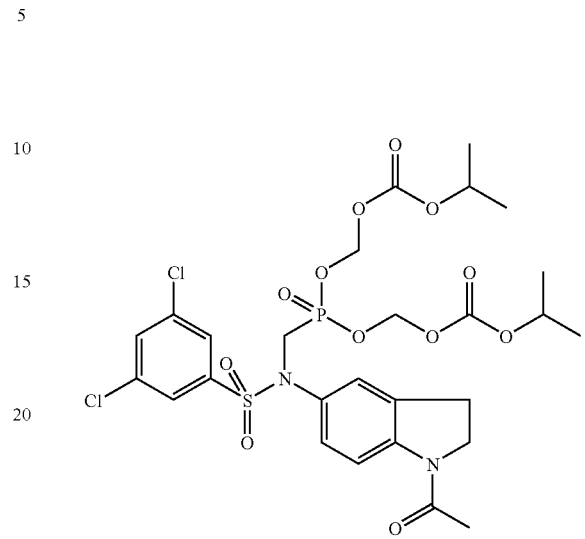

Mass spectrum (ESI+): m/z=728 [M+NH4]+

(3) diisopropoxycarbonyloxymethyl {[(3,5-dichloro-phenylsulphonyl)-(1-methylcarbamoyl-2,3-dihydro-1H-indol-5-yl)-amino]-methyl}-phosphonate

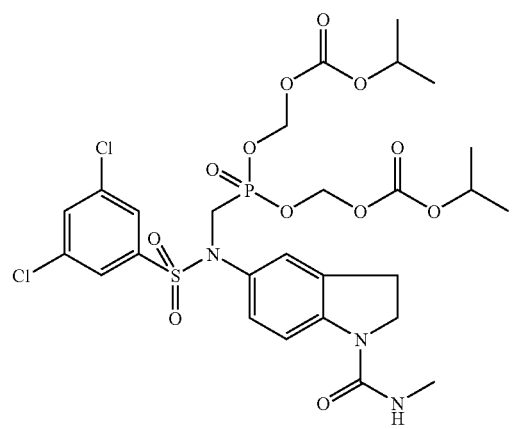

Mass spectrum (ESI+): m/z=743 [M+NH4]+

The following compounds are obtained analogously to the foregoing Examples and other methods known from the literature:

| No. | Name | Structural formula |
| --- | --- | --- |
| (1) | {[(3,5-dichloro-phenylsulphonyl)-(1-ethyl-2,3-dihydro-1H-indol-5-yl)-amino]-methyl}-phosphonic acid | |
| (2) | {[(1-benzyl-1H-indol-5-yl)-(3,5-dichloro-phenylsulphonyl)-amino]-methyl}-phosphonic acid | |
| (3) | {[(3,5-dichloro-phenylsulphonyl)-(1-propionyl-2,3-dihydro-1H-indol-5-yl)-amino]-methyl}-phosphonic acid | |
| (4) | {[(1-benzoyl-2,3-dihydro-1H-indol-5-yl)-(3,5-dichloro-phenylsulphonyl)-amino]-methyl}-phosphonic acid | |

| No. | Name | Structural formula |
|---|---|---|
| (5) | {[(1-carbamoyl-2,3-dihydro-1H-indol-5-yl)-(3,5-dichloro-phenylsulphonyl)-amino]-methyl}-phosphonic acid | |
| (6) | {[(3,5-dichloro-phenylsulphonyl)-(3-ethylcarbamoyl-1-methyl-1H-indazol-6-yl)-amino]-methyl}-phosphonic acid | |
| (7) | {[(3,5-dichloro-phenylsulphonyl)-(3-isopropylcarbamoyl-1-methyl-1H-indazol-6-yl)-amino]-methyl}-phosphonic acid | |
| (8) | {[(3,5-dichloro-phenylsulphonyl)-(3-diethylcarbamoyl-1-methyl-1H-indazol-6-yl)-amino]-methyl}-phosphonic acid | |

-continued

| No. | Name | Structural formula |
|---|---|---|
| (9) | {[(1-cyclopropylcarbamoyl-2,3-dihydro-1H-indol-5-yl)-(3,5-dichloro-phenylsulphonyl)-amino]-methyl}-phosphonic acid | |
| (10) | ({(3,5-dichloro-phenylsulphonyl)-[1-methyl-3-(pyrrolidine-1-carbonyl)-1H-indol-6-yl]-amino}-methyl)-phosphonic acid | |
| (11) | ({(3,5-dichloro-phenylsulphonyl)-[3-(3-hydroxy-pyrrolidine-1-carbonyl)-1-methyl-1H-indol-6-yl]-amino}-methyl)-phosphonic acid | |
| (12) | ({(3,5-dichloro-phenylsulphonyl)-[1-methyl-3-(piperidine-1-carbonyl)-1H-indol-6-yl]-amino}-methyl)-phosphonic acid | |

-continued

| No. | Name | Structural formula |
|-----|------|--------------------|
| (13) | ({(3,5-dichloro-phenylsulphonyl)-[1-methyl-3-(morpholine-4-carbonyl)-1H-indol-6-yl]-amino}-methyl)-phosphonic acid | |
| (14) | ({(3,5-dichloro-phenylsulphonyl)-[1-methyl-3-(piperazine-1-carbonyl)-1H-indol-6-yl]-amino}-methyl)-phosphonic acid | |
| (15) | ({(3,5-dichloro-phenylsulphonyl)-[1-(pyridin-3-ylcarbamoyl)-2,3-dihydro-1H-indol-5-yl]-amino}-methyl)-phosphonic acid | |
| (16) | {[(1-benzensulphonyl-2,3-dihydro-1H-indol-5-yl)-(3,5-dichloro-phenylsulphonyl)-amino]-methyl}-phosphonic acid | |

| No. | Name | Structural formula |
|---|---|---|
| (17) | {[(3,5-dichloro-phenylsulphonyl)-(1-phenylmethanesulphonyl-2,3-dihydro-1H-indol-5-yl)-amino]-methyl}-phosphonic acid | |
| (18) | {[(3-bromo-5-methyl-phenylsulphonyl)-(1-methylcarbamoyl-2,3-dihydro-1H-indol-5-yl)-amino]-methyl}-phosphonic acid | |

Example 3

Coated Tablets Containing 75 mg of Active Substance 1 tablet core contains:

| | |
|---|---:|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

Example 4

Tablets Containing 100 mg of Active Substance

Composition:

1 tablet contains:

| | |
|---|---:|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example 5

Tablets Containing 150 mg of Active Substance

Composition:
1 tablet contains:

| | |
|---|---:|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

Example 6

Hard Gelatine Capsules Containing 150 mg of Active Substance 1 capsule contains:

| | |
|---|---:|
| active substance | 150.0 mg |
| corn starch (dried | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.
Capsule filling: approx. 320 mg
Capsule shell: size 1 hard gelatine capsule.

Example 7

Suppositories Containing 150 mg of Active Substance 1 suppository contains:

| | |
|---|---:|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example 8

Suspension Containing 50 mg of Active Substance 100 ml of suspension contain:

| | |
|---|---:|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. Water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example 9

Ampoules Containing 10 mg Active Substance

Composition:

| | |
|---|---:|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Example 10

Ampoules Containing 50 mg of Active Substance

Composition:

| | |
|---|---:|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:
1. A compound of formula (I)

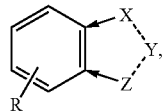
(I)

wherein
R denotes a group of formula

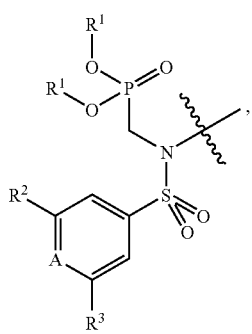

wherein
$R^1$ denotes H, $C_{1-6}$-alkyl-carbonyl-oxy-$C_{1-3}$-alkyl or $C_{1-6}$-alkoxy-carbonyl-oxy-$C_{1-3}$-alkyl,
$R^2$ and $R^3$ independently of one another denote H, halogen, $C_{1-3}$-alkyl, $C_{1-3}$-perfluoralkyl, $C_{1-3}$-perfluoroalkoxy, $C_{1-3}$-alkoxy, cyano, nitro or hydroxy
and
A denotes CH or N,
and the heterocyclic group

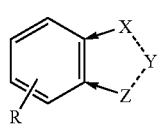

denotes a group of formula

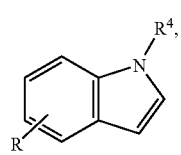
(Ia)

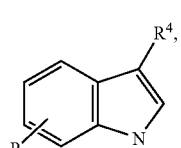
(Ib)

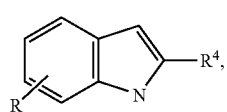
(Ic)

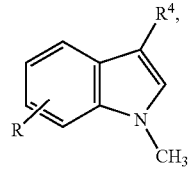
(Id)

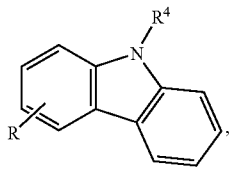
(Ie)

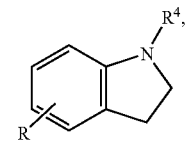
(If)

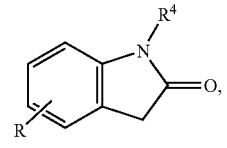
(Ig)

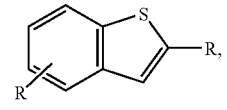
(Ih)

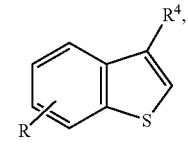
(Ii)

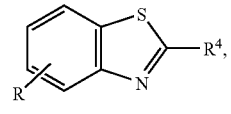
(Ij)

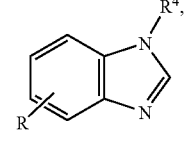
(Ik)

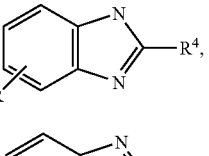
(Im)

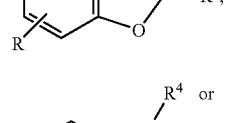
(In)

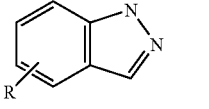
(Io)
or

-continued

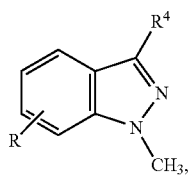
(Ip)

wherein the above-mentioned heterocycles of formula n (Ia), (Ib), (Ic), (Id), (If), (Ig), (Ih), (Ii), (Ik) and (Io) may optionally be substituted at the carbon atoms of the 5 ring in each case by a group selected from among $C_{1-3}$-alkyl, cyano, $C_{1-3}$-perfluoralkyl, $C_{3-6}$-cycloalkyl, $C_{1-3}$-alkyl-carbonyl, $C_{1-3}$-Perfluoralkyl-carbonyl, carboxyl, amino-methyl, $C_{1-3}$-alkyl-aminomethyl, di-($C_{1-3}$-alkyl)-aminomethyl, $C_{1-3}$-alkyl-carboxyl, carboxy-$C_{1-3}$-alkyl, aminocarbonyl, $C_{1-3}$-alkyl-aminocarbonyl or di-($C_{1-3}$-alkyl)-aminocarbonyl and $R^4$ denotes H, $C_{1-6}$-alkyl, $C_{1-6}$-alkyl-carbonyl, cyano, carboxyl, $C_{1-6}$-alkoxy-carbonyl, phenylcarbonyl, 5-chloro-1H-indol-2-yl-carbonyl, aminocarbonyl, $C_{1-6}$-alkyl-aminocarbonyl, di-($C_{1-6}$-alkyl)-aminocarbonyl, $C_{3-6}$-cycloalkyl-aminocarbonyl, N—($C_{3-6}$-cycloalkyl)-N—($C_{1-6}$-alkyl)-aminocarbonyl, morpholin-4-yl-carbonyl, piperazin-1-yl-carbonyl, 4-($C_{1-3}$-alkyl)-piperazin-1-yl-carbonyl, aryl-amino-carbonyl, N-oxy-pyridylamino-carbonyl, aminocarbonyl-carbonyl, $C_{1-3}$-alkylaminocarbonyl-carbonyl, di-($C_{1-3}$-alkyl)-aminocarbonyl-carbonyl, pyrrolidinylcarbonyl-carbonyl, piperidinylcarbonyl-carbonyl, morpholinylcarbonyl-carbonyl, piperazinylcarbonyl-carbonyl, 4-methyl-piperazin-1-ylcarbonyl-carbonyl, $C_{1-3}$-alkyl-sulphonyl or phenyl-sulphonyl, while the $C_{1-6}$-alkyl group mentioned above in the definition of $R^4$ may be substituted by phenyl or phenyl-sulphonyl, the $C_{1-6}$-alkyl-carbonyl group mentioned above in the definition of $R^4$ may be substituted in the alkyl moiety by di-($C_{1-3}$-alkyl)-amino, pyrrolidin-1-yl, piperidin-1-yl, morpholin-4-yl, piperazin-1-yl, 4-methyl-piperazin-1-yl or phenyl, the $C_{1-6}$-alkyl-aminocarbonyl, di-($C_{1-6}$-alkyl)-aminocarbonyl and N—($C_{3-6}$-cycloalkyl)-N—($C_{1-6}$-alkyl)-aminocarbonyl groups mentioned above in the definition of $R^4$ may each be substituted in the alkyl moiety by $C_{1-3}$-alkyl-amino, di-($C_{1-3}$-alkyl)-amino, $C_{3-6}$-cycloalkyl-amino, N—($C_{3-6}$-cycloalkyl)-N—($C_{1-6}$-alkyl)-amino, pyrrolidin-1-yl, piperidin-1-yl, morpholin-4-yl, piperazin-1-yl, 4-methyl-piperazin-1-yl or methylaminocarbonyl, the aryl moiety of the aryl-amino-carbonyl groups mentioned above in the definition of $R^4$ is a 6-membered aromatic system which contains 0 to 3 nitrogen atoms and may be substituted by nitro, the $C_{1-6}$-alkyl groups of the di-($C_{1-6}$-alkyl)-aminocarbonyl groups mentioned above in the definition of $R^4$, together with the nitrogen atom to which they are bound, may form a saturated 4- to 7-membered ring system, which may be substituted by hydroxy, and the $C_{1-3}$-alkyl-sulphonyl group mentioned above in the definition of $R^4$ may be substituted by phenyl in the alkyl moiety, or the tautomers, stereoisomers, mixtures thereof and salts thereof.

2. A compound of formula (I) according to claim 1, wherein

R denotes a group of the formula mentioned in claim 1, wherein $R^1$ denotes H, $C_{1-6}$-alkyl-carbonyl-oxy-$C_{1-2}$-alkyl or $C_{1-6}$-alkoxy-carbonyl-oxy-$C_{1-2}$-alkyl, $R^2$ and $R^3$ independently of one another denote halogen, $C_{1-3}$-alkyl, $C_{1-3}$-perfluoroalkyl, $C_{1-2}$-alkoxy or cyano and A denotes CH or N, and the heterocyclic group

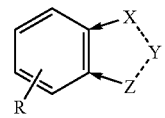

denotes a group of formula

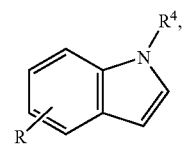
(Ia)

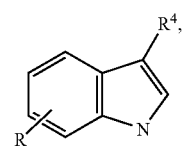
(Ib)

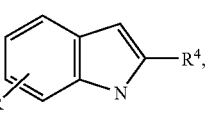
(Ic)

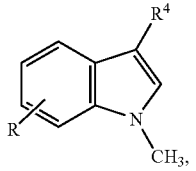
(Id)

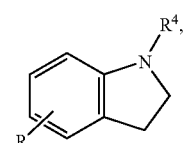
(If)

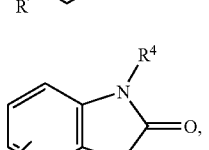
(Ig)

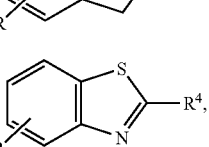
(Ij)

-continued

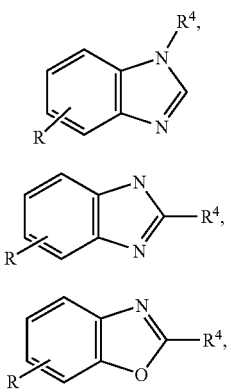

(Ik)

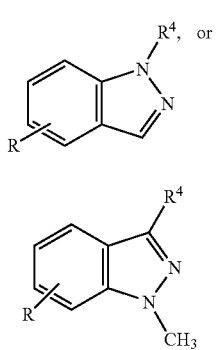

(Im)

(In)

(Io)

(Ip)

wherein the above-mentioned heterocycles of formulae (Ia), (If) and (Ig) may optionally be substituted at the carbon atoms of the 5 ring in each case by a group selected from among $C_{1-3}$-alkyl, $C_{1-3}$-alkyl-carbonyl or $C_{1-3}$-perfluoroalkyl-carbonyl and $R^4$ denotes H, $C_{1-4}$-alkyl, $C_{1-4}$-alkyl-carbonyl, cyano, carboxyl, $C_{1-4}$-alkoxy-carbonyl, phenylcarbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N—($C_{3-6}$-cycloalkyl)-N—($C_{1-4}$-alkyl)-aminocarbonyl, morpholin-4-yl-carbonyl, piperazin-1-yl-carbonyl, 4-(methyl)-piperazin-1-yl-carbonyl, N,N-di-($C_{1-4}$-alkyl)-amino-$C_{1-3}$-alkyl-amino-carbonyl, aryl-amino-carbonyl, $C_{1-2}$-alkyl-sulphonyl, phenyl-$C_{1-2}$-alkyl-sulphonyl or phenyl-sulphonyl, while the $C_{1-4}$-alkyl group mentioned above in the definition of $R^4$ may be substituted by phenyl, the $C_{1-4}$-alkyl-carbonyl group mentioned above in the definition of $R^4$ may be substituted in the alkyl moiety by morpholin-4-yl or phenyl, the aryl moiety of the aryl-amino-carbonyl groups mentioned above in the definition of $R^4$ is a 6-membered aromatic system which contains 0 to 2 nitrogen atoms, and the $C_{1-4}$-alkyl groups of the di-($C_{1-4}$-alkyl)-aminocarbonyl groups mentioned above in the definition of $R^4$ may form together with the nitrogen atom to which they are bound a saturated 4- to 6-membered ring system, which may be substituted by hydroxy, or the tautomers, stereoisomers, mixtures thereof and salts thereof.

3. A compound of formula (I) according to claim 2, wherein

R denotes a group of the above-mentioned formula, wherein
$R^1$ denotes H, $C_{1-4}$-alkyl-carbonyl-oxy-$C_{1-2}$-alkyl or $C_{1-4}$-alkoxy-carbonyl-oxy-$C_{1-2}$-alkyl,
$R^2$ and $R^3$ independently of one another represent chlorine, bromine or $C_{1-2}$-alkyl and
A denotes CH or N, and the heterocyclic group

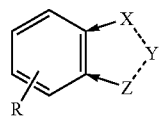

denotes a group of formula

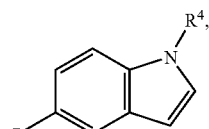

(Ia-1)

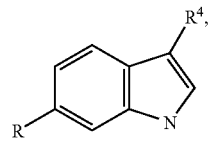

(Ib-1)

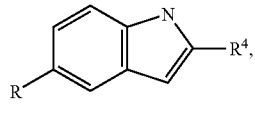

(Ic-1)

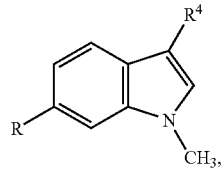

(Id-1)

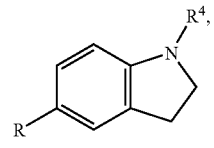

(If-1)

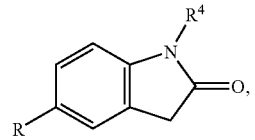

(Ig-1)

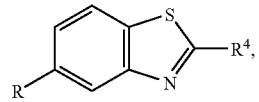

(Ij-1)

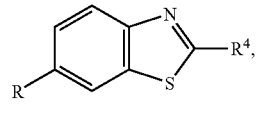

(Ij-2)

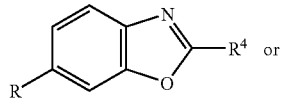

(In-1)

(Ip-1)

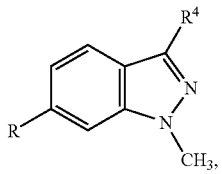

wherein the above-mentioned heterocycles of formulae (Ia) and (If) may optionally be substituted at the carbon atoms of the 5 ring in each case by a group selected from among methyl, ethyl, methylcarbonyl or trifluoromethylcarbonyl and $R^4$ denotes H, $C_{1-4}$alkyl, benzyl, $C_{1-4}$-alkyl-carbonyl, $C_{1-4}$-alkoxy-carbonyl, phenylcarbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N—($C_{3-6}$-cycloalkyl)-N—($C_{1-4}$-alkyl)-aminocarbonyl, pyrrolidin-1-yl-carbonyl, 3-hydroxy-pyrrolidin-1-yl-carbonyl, piperidin-1-yl-carbonyl, morpholin-4-yl-carbonyl, piperazin-1-yl-carbonyl, N,N-di-($C_{1-3}$-alkyl)-amino-$C_{1-3}$-alkyl-aminocarbonyl, phenylamino-carbonyl, pyridinylamino-carbonyl, aminocarbonyl-carbonyl, benzyl-sulphonyl or phenyl-sulphonyl, while the $C_{1-4}$-alkyl-carbonyl group mentioned above in the definition of $R^4$ may be substituted in the alkyl moiety by morpholin-4-yl, or the tautomers, stereoisomers, mixtures thereof and salts thereof.

4. A compound of formula (I) according to claim 3, wherein

R denotes a group of the above-mentioned formula, wherein $R^1$ denotes H, $C_{1-4}$-alkyl-carbonyl-oxy-methyl or $C_{1-4}$-alkoxy-carbonyl-oxy-methyl, $R^2$ and $R^3$ independently of one another represent chlorine, bromine or methyl and A denotes CH or N, and the heterocyclic group

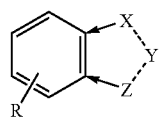

denotes a group of formula (Ia-1)

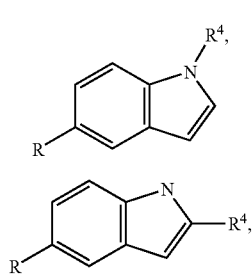

(Ic-1)

(Id-1)

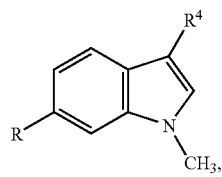

(If-1)

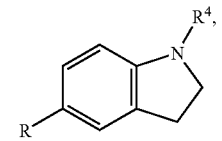

(Ig-1)

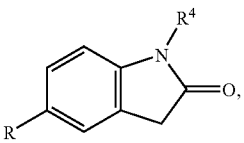

(Ij-1)

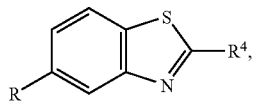

(Ij-2)

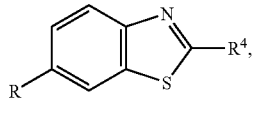

(In-1)

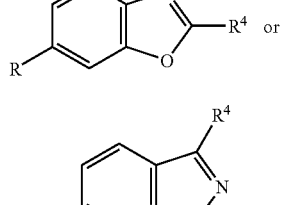 or (Ip-1)

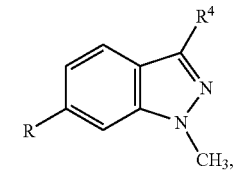

wherein $R^4$ denotes H, $C_{1-3}$-alkyl, benzyl, $C_{1-3}$-alkyl-carbonyl, morpholin-4-yl-methyl-carbonyl, $C_{1-2}$-alkoxy-carbonyl, phenylcarbonyl, 5-chloro-1H-indol-2-yl-carbonyl, amino-carbonyl, $C_{1-3}$-alkyl-aminocarbonyl, di-($C_{1-3}$-alkyl)-aminocarbonyl, cyclopropyl-amino-carbonyl, pyrrolidin-1-yl-carbonyl, 3-hydroxy-pyrrolidin-1-yl-carbonyl, piperidin-1-yl-carbonyl, morpholin-4-yl-carbonyl, piperazin-1-yl-carbonyl, N,N-dimethyl-amino-ethyl-amino-carbonyl, phenylamino-carbonyl, pyridinylamino-carbonyl, benzyl-sulphonyl or phenyl-sulphonyl, or the tautomers, stereoisomers, mixtures thereof and salts thereof.

5. A compound of formula (I) according to claim 4, wherein

R denotes a group of the formula mentioned in claim 1, wherein

R denotes a group of the above-mentioned formula, wherein $R^1$ denotes H, tert.-butyl-carbonyl-oxy-methyl or iso-propyloxy-carbonyl-oxy-methyl, $R^2$ and $R^3$ independently of one another represent chlorine, bromine or methyl and A denotes CH, and the heterocyclic group

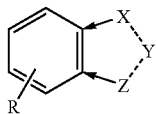

denotes a group of formula

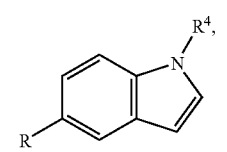 (Ia-1)

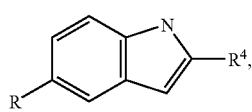 (Ic-1)

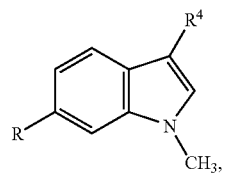 (Id-1)

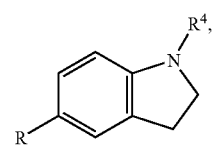 (If-1)

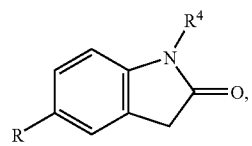 (Ig-1)

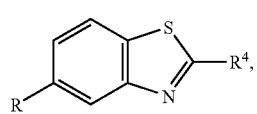 (Ij-1)

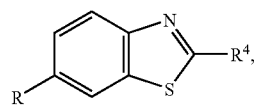 (Ij-2)

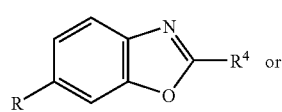 (In-1)

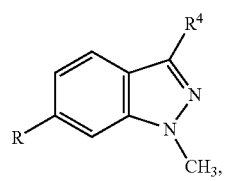 (Ip-1)

wherein $R^4$ denotes H, $C_{1-2}$-alkyl, benzyl, $C_{1-2}$-alkyl-carbonyl, morpholin-4-yl-methyl-carbonyl, ethoxycarbonyl, phenylcarbonyl, 5-chloro-1H-indol-2-yl-carbonyl, aminocarbonyl, $C_{1-3}$-alkyl-aminocarbonyl, di-($C_{1-2}$-alkyl)-aminocarbonyl, cyclopropyl-amino-carbonyl, pyrrolidin-1-yl-carbonyl, 3-hydroxy-pyrrolidin-1-yl-carbonyl, piperidin-1-yl-carbonyl, morpholin-4-yl-carbonyl, piperazin-1-yl-carbonyl, N,N-dimethyl-amino-ethyl-amino-carbonyl, phenylamino-carbonyl, pyridinylamino-carbonyl, benzyl-sulphonyl or phenyl-sulphonyl, or the tautomers, stereoisomers, mixtures thereof and salts thereof.

6. A compound of formula (I) according to claim 5, wherein

R denotes a group of the above-mentioned formula, wherein $R^1$ denotes H, tert.-butyl-carbonyl-oxy-methyl or iso-propyloxy-carbonyl-oxy-methyl, $R^2$ and $R^3$ independently of one another denote chlorine or methyl and A denotes CH, and the heterocyclic group

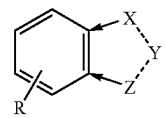

denotes a group of formula

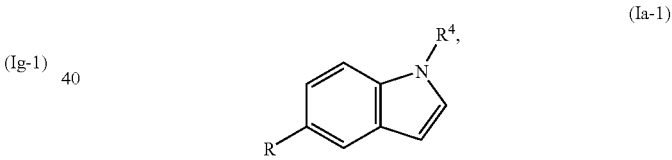 (Ia-1)

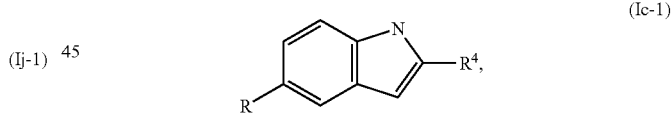 (Ic-1)

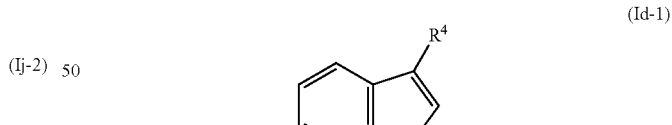 (Id-1)

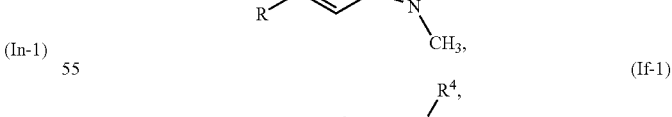 (If-1)

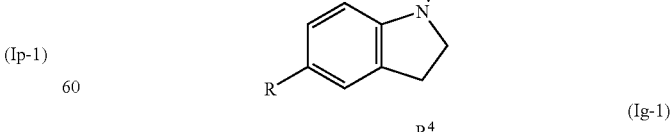 (Ig-1)

-continued

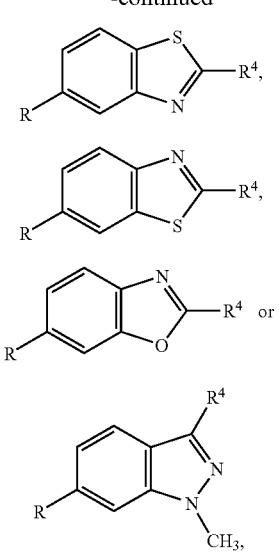

(Ij-1)

(Ij-2)

(In-1)

(Ip-1)

wherein
R⁴ denotes H, $C_{1-2}$-alkyl, $C_{1-2}$-alkyl-carbonyl, morpholin-4-yl-methyl-carbonyl, ethoxy-carbonyl, 5-chloro-1H-indol-2-yl-carbonyl, aminocarbonyl, $C_{1-2}$-alkyl-aminocarbonyl, di-($C_{1-2}$-alkyl)-aminocarbonyl, pyrrolidin-1-yl-carbonyl, N,N-dimethyl-amino-ethyl-aminocarbonyl or phenylamino-carbonyl, or the tautomers, stereoisomers, mixtures thereof and salts thereof.

7. A compound according to claim 1 selected from:
(1) {[(3,5-dichloro-phenylsulphonyl)-(1-methyl-2-oxo-2,3-dihydro-1H-indol-5-yl)-amino]-methyl}-phosphonic acid,
(2) {[(3,5-dichloro-phenylsulphonyl)-(2-oxo-2,3-dihydro-1H-indol-5-yl)-amino]-methyl}-phosphonic acid,
(3) {[(1-acetyl-2,3-dihydro-1H-indol-5-yl)-(3,5-dichloro-phenylsulphonyl)-amino]-methyl}-phosphonic acid,
(4) {[(3,5-dichloro-phenylsulphonyl)-(1-methylcarbamoyl-2,3-dihydro-1H-indol-5-yl)-amino]-methyl}-phosphonic acid,
(5) {[(1-acetyl-2,3-dihydro-1H-indol-5-yl)-(3,5-dichloro-phenylsulphonyl)-amino]-methyl}-(2,2-dimethyl-propionyloxymethoxy)-phosphinoyloxymethyl 2,2-dimethyl-propionate and
(6) diisopropoxycarbonyloxymethyl {[(1-acetyl-2,3-dihydro-1H-indol-5-yl)-(3,5-dichloro-phenylsulphonyl)-amino]-methyl}-phosphonate, or the enantiomers thereof, the mixtures thereof and the salts thereof.

8. A physiologically acceptable salt of the compound according to claim 1 with an inorganic or organic acid or base.

9. A method of using a compound according to claim 1 for the treatment of type I and type II diabetes mellitus.

10. A pharmaceutical composition containing a compound according to claim 1, or a salt thereof, optionally together with one or more inert carriers and/or diluents.

11. Process for preparing a pharmaceutical composition characterised in that a compound according to claim 1, or a salt thereof, is incorporated in one or more inert carriers and/or diluents by a non-chemical method.

12. Process for preparing a compound of formula (I) according to claim 1, characterised in that
a compound of general formula (IV)

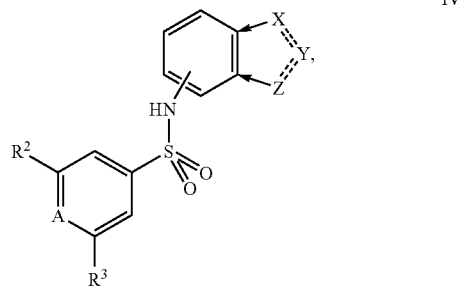

IV wherein $R^2$, $R^3$, X, Y, Z and A are defined as in claim 1, is alkylated by means of a compound of general formula $(R^1-O-)_2P(=O)-CH_2-X$, wherein X denotes a leaving group,
and
if desired any protective group used to protect reactive groups during the reactions is cleaved afterwards or simultaneously and/or
a compound of general formula I thus obtained is resolved into its stereoisomers and/or a compound of general formula I thus obtained is converted into a salt with an inorganic or organic acid or base.

* * * * *